(12) United States Patent
Khan

(10) Patent No.: US 8,133,733 B2
(45) Date of Patent: *Mar. 13, 2012

(54) NONVIRAL VECTORS FOR DELIVERING POLYNUCLEOTIDES TO TARGET TISSUES

(75) Inventor: Shaharyar Khan, Charlottesville, VA (US)

(73) Assignee: Gencia Corporation, Charlottesville, VA (US)

( * ) Notice: Subject to any disclaimer, the term of this patent is extended or adjusted under 35 U.S.C. 154(b) by 827 days.

This patent is subject to a terminal disclaimer.

(21) Appl. No.: 11/932,674

(22) Filed: Oct. 31, 2007

(65) Prior Publication Data

US 2009/0227655 A1 Sep. 10, 2009

Related U.S. Application Data

(63) Continuation-in-part of application No. 10/972,963, filed on Oct. 25, 2004, now Pat. No. 8,039,587.

(60) Provisional application No. 60/513,983, filed on Oct. 24, 2003, provisional application No. 60/568,436, filed on May 5, 2004.

(51) Int. Cl.
*C12N 15/00* (2006.01)
*C07K 14/00* (2006.01)
*C07K 14/435* (2006.01)
*C12Q 1/68* (2006.01)

(52) U.S. Cl. ... 435/455; 435/468; 530/350; 530/388.21; 530/300

(58) Field of Classification Search .......... None
See application file for complete search history.

(56) References Cited

U.S. PATENT DOCUMENTS

| | | | | |
|---|---|---|---|---|
| 5,804,445 A * | 9/1998 | Brasier | ......... | 435/375 |
| 5,831,020 A | 11/1998 | Citovsky | | |
| 6,017,734 A * | 1/2000 | Summers et al. | ......... | 435/69.7 |
| 6,127,159 A | 10/2000 | Fuller et al. | | |
| 6,506,559 B1 | 1/2003 | Driver et al. | ......... | 435/6 |
| 6,531,647 B1 | 3/2003 | Baulcombe et al. | ......... | 800/278 |
| 6,759,574 B1 | 7/2004 | Ream, Jr. et al. | ......... | 800/301 |
| 6,835,810 B2 | 12/2004 | Hwu | | |
| 6,903,077 B1 | 6/2005 | Heintz | | |
| 7,001,768 B2 * | 2/2006 | Wolffe | ......... | 435/375 |
| 2002/0086356 A1 | 7/2002 | Tuschl et al. | ......... | 435/69.1 |
| 2002/0132990 A1 * | 9/2002 | Huston et al. | ......... | 530/391.1 |
| 2002/0155095 A1 * | 10/2002 | Nagabhushan et al. | ..... | 424/93.1 |
| 2003/0104622 A1 | 6/2003 | Robbins et al. | ......... | 435/455 |
| 2003/0186233 A1 | 10/2003 | Chesnut et al. | | |
| 2003/0237112 A1 | 12/2003 | Brown et al. | | |
| 2004/0009922 A1 | 1/2004 | Mochly-Rosen | | |
| 2004/0072739 A1 | 4/2004 | Anderson et al. | | |
| 2004/0101874 A1 | 5/2004 | Ghosh | | |
| 2004/1009187 | 5/2004 | Sera | | |
| 2004/0176282 A1 | 9/2004 | Dalby et al. | | |
| 2005/1001583 | 1/2005 | Dorokhov et al. | | |
| 2005/0042603 A1 | 2/2005 | Wang | | |
| 2005/0147993 A1 | 7/2005 | Khan | | |
| 2006/0211647 A1 | 9/2006 | Khan | | |
| 2007/0196334 A1 | 8/2007 | Khan | | |
| 2008/0222750 A1 | 9/2008 | Khan | | |
| 2009/1012346 | 5/2009 | Khan | | |
| 2009/0208478 A1 | 8/2009 | Khan | | |
| 2009/0227655 A1 | 9/2009 | Khan | | |

FOREIGN PATENT DOCUMENTS

| | | |
|---|---|---|
| CA | 2272788 | 12/2000 |
| DE | 198 56 052 | 6/2000 |
| KR | 20030012226 | 2/2003 |
| WO | WO 97/27742 | 8/1997 |
| WO | WO 98/46271 | 10/1998 |
| WO | WO 9856938 | 12/1998 |
| WO | WO 00/19993 | 4/2000 |
| WO | WO 00/012732 | 9/2000 |
| WO | WO 00/58488 | 10/2000 |
| WO | 03025195 | 3/2003 |
| WO | WO 03/025195 | 3/2003 |
| WO | WO 03/052067 | 6/2003 |
| WO | WO 03/076561 | 9/2003 |
| WO | WO 2004/061456 | 7/2004 |
| WO | 2005003766 | 1/2005 |
| WO | WO 2005/056752 | 6/2005 |
| WO | 2008072781 | 5/2008 |
| WO | WO 01/75164 A2 | 10/2011 |

OTHER PUBLICATIONS

Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Bayona-Bafaluy, "Rapid directional shift of mitochondrial DNA heteroplasmy in animal tissues by a mitochondrially targeted restriction endonuclease,"*Proc. Natl. Acad. Sci. U S A*. 102(40):14392-7(2005).
D'Souza "Gene therapy of the other genome: the challenges of treating mitochondrial DNA defects" *Pharm Res*. 24(2):228-38(2007).
Del Gaizo, "A novel TAT-mitochondrial signal sequence fusion protein is processed, stays in mitochondria, and crosses the placenta,"*Mol. Ther*. 7(6):720-30(2003).
Flierl, "Targeted delivery of DNA to the mitochondrial compartment via import sequence-conjugated peptide nucleic acid," *Mol. Ther*, 7(4):550-7(2003).
Khan, "Development of mitochondrial gene replacement therapy," *J. Bioenergetics and Biomembranes* 36L387-393(2004).
Maliga, "Plant Biotechnology 2007: all three genomes make contributions to progress" *Current Opinion in Biotech*. 18:97-99(2007).
Murphy, "Selective Targeting of Bioactive Compounds to Mitochondria," *Trends in Biotech*. 15(8):326-30(1997).
Seibel, "Transfection of mitochondria: strategy towards a gene therapy of mitochondrial DNA diseases," *Nucleic Acids Res*. 23(1):10-17(1995).
Shore, "Import and insertion of proteins into the mitochondrial outer membrane" *Eur. J. Biochem*. 227:9-18(1995).
Sloots, "Recombinant derivatives of the human high-mobility group protein HMGB2 mediate efficient nonviral gene delivery" *FEBS* 272:4221-4236(2005).
Srivastava, "Manipulating mitochondrial DNA heteroplasmy by a mitochondrially targeted restriction endonuclease," *Hum. Mol. Genet*.10(26):3093-9(2001).

(Continued)

*Primary Examiner* — Maria Marvich

(74) *Attorney, Agent, or Firm* — Pabst Patent Group LLP

(57) ABSTRACT

Methods and compositions for delivering polynucleotides are provided. One embodiment provides a non-viral vector comprising a recombinant polynucleotide-binding protein comprising a protein transduction domain operably linked to a targeting signal.

10 Claims, No Drawings

OTHER PUBLICATIONS

Tanaka, "Gene therapy for mitochondrial disease by delivering restriction endonuclease SmaI into mitochondria," *J. Biomed. Sci.* 9(6 Pt 1):534-41(2002).

Vestweber, "DNA-protein conjugates can enter mitochondria via the protein import pathway," *Nature* 338(6211):170-2(1989).

Anziano and Butow, "Splicing-defective mutants of the yeast mitochondrial COXI gene can be corrected by transformation with a hybrid maturase gene", *Proc. Natl. Acad. Sci. U.S.A.*, 118(13):5592-6 (1991).

Bhat and Epelboym, "Quantitative analysis of total mitochondrial DNA: competitive polymerase chain reaction versus real-time polymerase chain reaction", *J. Biochem. Mol. Toxicol.*, 18(4180-6 (2004).

Carrozzo, et al., "Maternally-inherited Leigh syndrome-related mutations bolster mitochondrial-mediated apoptosis", *J. Neurochem*, 90(21:490-501 (2004).

Cervin, et al., "Cosegregation of MIDD and MODY in a pedigree: functional and clinical consequences", *Diabetes*, 53(7):1894-9 (2004).

Chen, et al., "Determination of normal ranges of mitochondrial respiratory activities by mtDNA transfer from 54 Human subjects to mDNA-less HeLa cells for identification of the pathogenicities of mutated mtDNAs", *J. Biochem.* (Tokyo), 135(2):237-43, 2004.

Claros and Vincens, "Computational method to predict mitochondrially imported proteins and their targeting sequences", *Eur. J. Biochem.*, 241(3):779-86 (1996).

D'Souza, et al., "DOAsome-mediated delivery of plasmid DNA toward mitochondria in living cells", *J.Control. Release*, 92(121:189-97 (2003).

Falkenberg, et al., "Mitochondrial transcription factors B1 and B2 activate transcription of human mtDNA", *Nat. Genet.*, 31(3):289-94 (2002).

Grosschedl, et al., "HMG domain proteins: architectural elements in the assembly of nucleoprotein structures", *Trends Genet.*, 10(3):94-100 (1994).

Guy, et al., "Rescue of a mitochondrial deficiency causing Leber Hereditary Optic Neuropathy", *Ann. Neurol.*, 52(51:534-42 (2002).

Ignatovich, et al., "Complexes of plasmid DNA with basic domain 47-57 of the HIV-1 Tat protein are transferred to mammalian cells by endocytosis-mediated pathways", *J. Biol. Chem.*, 278(43):42625-36 (2003).

Khadake and Rao, "Condensation of DNA and chromatin by an SPKK-containing octapeptide repeat motif present in the C-terminus of histone H1", *Biochemistry*, 36(5):1041-51 (1997).

Levy, et al, "Cytoplasmic transfer in oocytes: biochemical aspects", *Hum. Reprod. Update*, 10(3):241-50 (2004).

Liu, et al, "Mitochondrial DNA mutation and depletion increase the susceptibility of human cells to apoptosis", *Ann. N.Y. Acad. Sci.*, 1011:133-45 (2004).

Lu and Hansen, "Revisiting the structure and functions of the linker histone C-terminal tail domain", *Biochem. Cell Biol.*, 81(3):173-6 (2003).

Luo and Saltzman, "Synthetic DNA delivery systems", *Nat. Biotechnol.*, 18(1):33-7 (2000).

Neupert, "Protein import into mitochondria", *Anna Rev. Biochem.*, 66:863-917 (1997).

Oca-Cossio, et al., "Limitations of allotopic expression of mitochondrial genes in mammalian cells", *Genetics*, 165(21:707-20 (2003).

Petros, et al., "mtDNA mutations increase tumorigenicity in prostate cancer", *Proc. Natl. Acad. Sci. U.S.A.*, 102(31:719-24 (2005).

Pineau, et al., "Targeting the NAD7 subunit to mitochondria restores a functional complex I and a wild type phenotype in the *Nicotine sylvestris* CMS II mutant lacking nad7", *J. Biol. Chem.*, 280(28):25994-6001 (2005).

Prosite Documentation PDOC00305, "HMG boxes A and B and DNA-binding domains signature and profile", updated Dec. 2004.

Rantanen and Larsson, "Regulation of mitochondrial DNA copy number during spermatogenesis", *Hum. Reprod.*, 15 Suppl 2:86-91 (2000).

Ross and Murphy, "Cell-penetrating peptides are excluded from the mitochondrial matrix", *Biochem. Soc. Trans.*, 32(Pt 6):1072-4 (2004).

Rossignol, et al., "Mitochondrial threshold effects", *Biochem. J.*, 370(Pt 3):751-62 (2003).

Roubertoux, et al., "Mitochondrial DNA modifies cognition in interaction with the nuclear genome and age in mice", *Nat. Genet.*, 35(1):65-9 (2003).

Roucou, et al., "Bioenergetic and structural consequences of allotopic expression of subunit 8 of yeast mitochondrial ATP synthase. The hydrophobic character of residues 23 and 24 is essential for maximal activity and structural stability of the enzyme complex", *Eur. J. Biochem.*, 261(2):444-51 (1999).

Schaefer, et al., "The epidemiology of mitochondrial disorders—past, present and future", *Biochim. Biophys. Acta*, 1659(2-3)115-20 (2004).

Seibel, et al., "Transfection of mitochondria: strategy towards a gene therapy of mitochondrial DNA diseases", *Nucleic Acids Res.*, 23(1):10-7 (1995).

Smigrodzki and Khan, "Mitochondrial microheteroplasmy and a theory of aging and age-related disease", *Rejuvenation Res.*, 8(3)172-98 (2005).

Srivastava and Moraes, "Manipulating mitochondrial DNA heteroplasmy by a mitochandrially targeted restriction endonuclease", *Hum. Mol. Genet.*, 10(26):3093-9 (2001).

Stephens and Pepperkok, "The many ways to cross the plasma membrane", *Proc. Natl. Acad. Sci. U.S.A.*, 98(8):4295-8 (2001).

Subirana, "Analysis of the charge distribution in the C-terminal region of histone H1 as related to its interaction with DNA", *Biopolymers*, 29(10-11):1351-7 (1990).

Suzuki, et al, "An NMR study on the DNA-binding SPKK motif and a model for its interaction with DNA", *Protein Eng.*, 6(6):565-74 (1993).

Suzuki, et al., "Maternal inheritance of diabetes is associated with inactive ALDH2 genotype in diabetics with renal failure in Japanese", *Diabetes Res. Clin. Pract.*, 60(2):143-5 (2003).

Tanaka, et al, "Gene therapy for mitochondrial disease by delivering restriction endonuclease SmaI into mitochondria", *J. Blamed. Sci.*, 9(6 Pt 1):534-41 (2002).

Taylor, et al., "Mitochondrial DNA mutations in human colonic crypt stem cells", *J. Clin. Invest.*, 112(9):1351-60 (2003).

Wang, et al., "Acquisition of double-stranded DNA-binding ability in a hybrid protein between *Escherichia coli* CspA and the cold shock domain of human YB-1", *Mol. Microbiol.*, 38(3):526-34 (2000).

Vestweber and Schatz, "DNA-protein conjugates can enter mitochondria via the protein import pathway", *Nature*, 338(6211):170-2 (1989).

Weir, et al, "Structure of the HMG box motif in the B-domain of HMG1", *EMBO J.*, 12(4):1311-9 (1993).

Zullo, et al, "Stable transformation of CHO Cells and human NARP cybrids confers oligomycin resistance (oli(r)) following transfer of a mitochondrial DNA-encoded oli(r) ATPase6 gene to the nuclear genome: a model system for mtDNA gene therapy", *Rejuvenation Res.*, 8(1):18-28 (2005).

Chinnery, et al., "Peptide nucleic acid delivery to human mitochondria", *Gene Ther.*, 6(12):1919-28 (1999).

Flierl, et al., "Targeted delivery of DNA to the mitochondrial compartment via import sequence conjugated peptide nucleic acid", *Mol. Ther.*, 7(4):550-7 (2003).

Muratovska, et al., "Targeting peptide nucleic acid (PNA) oligomers to mitochondria within cells by conjugation to lipophilic cations: implications for mitochondrial DNA replication, expression and disease", *Nucleic Acids Res.*, 29(9):1852-63 (2001).

Ross et al., "Cell-penetrating peptides do not cross mitochondrial membranes even when conjugated to a lipophilic cation: evidence against direct passage through phospholipid bilayers", *Biochem. J.*, 383(Pt. 3):457-68 (2004).

Smith, et al., "Delivery of bioactive molecules to mitochondria in vivo", *Proc. Natl. Acad. Sci. U.S.A.*, 100(9):5407-12 (2003).

U.S. Appl. No. 10/561,829, filed Dec. 21, 2005, Khan.

Alam, et al., "Human mitochondrial DNA is packaged with TFAM", *Nucleic Acids Res.*, 31(6):1640-5 (2003).

Cline and Henry "Import and routing of nucleus-encoded chloroplast proteins", *Annu. Rev. Cell Dev. Biol.*, 12:1-26 (1996).
Derossi, et al., "The third helix of the Antennapedia homeodomain translocates through biological membranes", *J. Biol. Chem.*, 269(14):10444-50 (1994).
Emanuelsson, et al., "Predicting subcellular localization of proteins based on their N-terminal amino acid sequence", *J. Mol. Biol.*, 300(4):1005-16 (2000).
Frankel and PABD, "Cellular uptake of the tat protein from human immunodeficiency virus", *Cell*, 55(6):1189-93 (1988).
Ho, et al., "Synthetic protein transduction domains enhanced transduction potential in vitro and in vivo", *Cancer Res.*, 61(2):474-7 (2001).
Kabouridis, "Biological applications of protein transduction technology", *Trends Biotechnol.*, 21(11):498-503 (2003).
Murphy, "Selective targeting of bioactive compounds to mitochondria", *Trends Biotechnol.*, 15(8);326-30 (1997).
Sandman, et al., "Diversity of prokaryotic chromosomal proteins and the origin of the nucleosome", *Cell. Mol. Life Sci.*, 54(12):1350-84 (1998).
Weissig, "Mitochondrial pharmaceutics", *Mitochondrion*,3(4):229-44 (2004).
Wender, et al., "The design, synthesis, and evaluation of molecules that enable or enhance cellular uptake: peptoid molecular transporters", *Proc. Natl. Acad. Sci. U.S.A.*, 97(24):13003-6 (2000).
Gaizo et al., (2003) "A Novel TAT-Mitochondrial Signal Sequence Fusion Protein Is Processed, Stays in Mitochondria, and Crosses the Placenta" *Molecular Therapy* vol. 7, No. 6, pp. 720-730.
Gaizo et al., (2003) "Targeting proteins to mitochondria using TAT", *Molecular Genetics and Metabolism 80* pp. 170-180.
Fortunati et al, A multi-domain protein for b1 integrin-targeted DNA delivery, Gene Therapy (2000) 7, 1505-1515.
Krueger et al, Peripheral-type benzodiazepine receptors mediate translocation of cholesterol from outer to inner mitochondrial membranes in adrenocortical cells, J. Biol. Chem., vol. 265, Issue 25, 15015-15022, Sep. 1990.
Futaki et al, Arginine-rich Peptides, The Journal of Biological Chemistry vol. 276, No. 8, Issue of Feb. 23, pp. 5836-5840, 2001.
Noguchi et al, Protein transduction technology offers a novel therapeutic approach for diabetes, J Hepatobiliary Pancreat Surg (2006) 13:306-313.
Suarez, et al., "Alterations in mitochondrial function and cytosolic calcium induced by hyperglycemia are restored by mitochondrial transcription factor A in cardiomyoctes", *Am. J. Physiol., Cell Physiol.*, 295:C1561-1568 (2008).
Blanchi, "Prokaryotic HU and eukaryotic HMG1: a kinked relationship" Molecular Microbiology, 14(1):1-5 1994.
Brydges, et al., "Mutation of an unusual mitochondrial targeting sequences of SODB2 produces multiple targeting fates in *Toxoplasma gondii*", J. Cell Science, 116(22):4675-85 (2003).
Chang, et al., "Cellular internalization of fluorescent proteins via arginine-rich intracellular delivery peptide in plant cells", Plant Cell Physiol., 46(3):482-488 (2005).
Dietz and Schooner, "Advances in Phytoremediation", Enviro. Health Petspectives, 109(Supp 1):163-18 (2001).
Genbank, Accession No. NM 003201, "*Homo sapiens* transcription factor A, mitochondrial (TFAM), nuclear gene encoding mitochondrial protein, mRNA", 4 pages, First available Mar. 24, 1999, accessed Sep. 8, 2009.
Genbank, Accession No. NM 005035, "*Homo sapiens* polymerase (RNA) mitochondrial (DNA directed) pseudogene 1 (POLRMTP1) on chromosome 17", 5 pages, First available May 14, 1999, accessed Sep. 8, 2009.
Glover and Lindsay, "Targeting proteins to mitochondria: a current overview", Biochem. J., 284:609-20 (1992).
Laudet, et al., "Ancestry and diversity of the HMG box superfamily", Nue. Acids Res., 21(10):2493-2501 (1993).
Lebedeva and Stein, "Antisense Oligonucleotides: Promise and Reality" Annu. Rev. Pharmacol. Toxicol., 41:403-19 (2001).
Mahata, "Functional delivery of a cytosolic tRNA into mutant mitochondria of human cells", Science, 314:471-74 (2006).
Rizzuto, et al., "Chimeric green fluorescent protein as a tool for visualizing subcellular organelles in living cells", Current Biology, 5(6):635-642 (1995).
Roberts, "Fast-track applications: The potential for direct delivery of proteins and nucleic acids to plant cells for the discovery of gene function", Plant Methods, 1:12 (2005).
Xin, et al., "DNA binding by single HMG box model proteins", Nucleic Acids Res., 28(20) 4044-50 (2000).
Dairaghi, et al., "Addition of a 29 residue carboxyl-terminal tail converts a simple HMG box-containing protein into a transcriptional activator", J Mol. Biol., 249:11-28 (1995).
Tiranti, et al., "Chromosomal localization of mitochondrial transcription factor A (TCF6), single-stranded DNA-binding protein (SSBP), and endonuclease G (ENDOG), three human housekeeping genes involved in mitochondrial biogenesis", Genomics, 25(2):559-64 (1995).vbTab.
Bustin, et al., "Recombinant human chromosomal proteins HMG-14 and HMG-17", Nucleic Acids Res., 19(11):3115-21 (1991).
Dement, et al., "Dynamic mitochondrial localization of nuclear transcription factor HMGA1", Exp Cell Res. 307(2):388-401 (2005).
Fischer, et al., "Cellular delivery of impermeable effector molecules in the form of conjugates with peptides capable of mediating membrane translocation", Bioconjug. Chem., 12(6):825-41 (2001).
Fisher, et al, "Promoter selection in human mitochondria involves binding of a transcription factor to orientation-independent upstream regulatory elements", Cell, 50(2):247-58 (1987).
GenBank, "Accession No. AF151833" (PRI May 18, 2000, direct submission May 17, 1999).
GenBank, "Accession No. AK026835" (PRI Sep. 12, 2006, direct submission Aug. 29, 2000).
GenBank, "Accession No. NM_003201" (PRI Sep. 3, 2009).
GenBank, "Accession No. NM_005035" (PRI Mar. 29, 2009).
Matsushima, et al., "Functional domains of chicken mitochondrial transcription factor A for the maintenance of mitochondrial DNA copy number in lymphoma cell line DT40", J. Biol. Chem., 278(33)21149-58 (2003).
Mistry, et al., "Recombinant HMG1 protein produced in *Pichia pastoris*: a nonviral gene delivery agent", Biotechniques, 22(4)718-29 (1997).
Porkka, et al., "A fragment of the HMGN2 protein homes to the nuclei of tumor cells and tumor endothelial cells in vivo", Proc. Natl. Acad. Sci. USA, 99(11):7444-9 (2002).
Tiranti, et al., "Identification of the gene encoding the human mitochondrial RNA polymerase (h-mtRPOL) by cyberscreening of the Expressed Sequence Tags database", Hum. Mel. Genet., 6(4):615-25 (1997).
Uherek & Wels, "DNA-carrier proteins for targeted gene delivery", Adv. Drug Deily. Rev. 44(2-3):153-66 (2000).
Wagner, et al, "Targeting of polyplexes: toward synthetic virus vector systems", Adv Gen, 53:333-354 (2005).
Zaitsev, et al., "H1 and HMG17 extracted from calf thymus nuclei are efficient DNA carriers in gene transfer", Gene Ther. 4(6):586-92 (1997).
Opalanska, et al., "Nucleic-acid therapeutics: basic principles and recent applications", Nat. Rev. Drug. Dis., 1:503-514 (2002).
Russell, "Replicating vectors for gene therapy of cancer: risks, limitations and prospects", Eur. J. Cancer, 30A(8):1165-1171 (1994).
Sandig, et al., Direct gene transfer of HMG1 based DNA-protein complexes, J. Mol. Med., 73:B10 (1995) (Abstract).
Schrank, "Functional expression of the yeast Mn-superoxide dismutase gene in *Escherichia coli* requires deletion of the signal peptide sequence", Gene, 73(1):121-30 (1988).
Kanki, et al., "Architectural role of mitochondrial transcription factor A in maintenance of human mitochondrial DNA," Mol. Cell. Biol., 24(22): 9823-9834 (2004).
McCullouch and Shadel, "Human mitochondrial transcription factor B1 interacts with the C-terminal activation region of h-mtTFA and stimulates transcription independently of its RNA methyltransferase activity," Mol. Cell. Biol., 23(16): 5816-5824 (2003).
Scarpulla, "Transcriptional paradigms in mammalian mitochondrial biogenesis and function," Physiol. Rev., 88: 611-638 (2008).
Jacobs, et al., "Making mitochondrial mutants", Trends in Genetics, 17(11):653-660 (2001).

* cited by examiner

```
                        SEQUENCE LISTING

<160> NUMBER OF SEQ ID NOS: 23

<210> SEQ ID NO 1
<211> LENGTH: 11
<212> TYPE: PRT
<213> ORGANISM: Human immunodeficiency virus

<400> SEQUENCE: 1

Tyr Gly Arg Lys Lys Arg Arg Gln Arg Arg Arg
1               5                   10

<210> SEQ ID NO 2
<211> LENGTH: 9
<212> TYPE: PRT
<213> ORGANISM: Human immunodeficiency virus

<400> SEQUENCE: 2

Arg Lys Lys Arg Arg Gln Arg Arg Arg
1               5

<210> SEQ ID NO 3
<211> LENGTH: 7
<212> TYPE: PRT
<213> ORGANISM: artificial sequence
<220> FEATURE:
<223> OTHER INFORMATION: AP-1 concensus site

<400> SEQUENCE: 3

Thr Gly Ala Cys Thr Cys Ala
1               5

<210> SEQ ID NO 4
<211> LENGTH: 16
<212> TYPE: PRT
<213> ORGANISM: Drosophila melanogaster

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 86
<212> TYPE: PRT
<213> ORGANISM: HIV

<400> SEQUENCE: 5
```

-continued

```
Met Glu Pro Val Asp Pro Arg Leu Glu Pro Trp Lys His Pro Gly Ser
 1               5                  10                 15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Glu Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85
```

<210> SEQ ID NO 6
<211> LENGTH: 7
<212> TYPE: PRT
<213> ORGANISM: artificial sequence
<220> FEATURE:
<223> OTHER INFORMATION: protein transduction domain

<400> SEQUENCE: 6

```
Arg Arg Arg Arg Arg Arg Arg
 1               5
```

<210> SEQ ID NO 7
<211> LENGTH: 12
<212> TYPE: PRT
<213> ORGANISM: artificial sequence
<220> FEATURE:
<223> OTHER INFORMATION: protein transduction domain

<400> SEQUENCE: 7

```
Arg Arg Gln Arg Arg Thr Ser Lys Leu Met Lys Arg
 1               5                  10
```

<210> SEQ ID NO 8
<211> LENGTH: 27
<212> TYPE: PRT
<213> ORGANISM: artificial sequence
<220> FEATURE:
<223> OTHER INFORMATION: protein transduction domain

<400> SEQUENCE: 8

```
Gly Trp Thr Leu Asn Ser Ala Gly Tyr Leu Leu Gly Lys Ile Asn Leu
 1               5                  10                 15

Lys Ala Leu Ala Ala Leu Ala Lys Lys Ile Leu
            20                  25
```

<210> SEQ ID NO 9
<211> LENGTH: 33
<212> TYPE: PRT
<213> ORGANISM: artificial sequence
<220> FEATURE:
<223> OTHER INFORMATION: synthetic sequence

<400> SEQUENCE: 9

```
Lys Ala Leu Ala Trp Glu Ala Lys Leu Ala Lys Ala Leu Ala Lys Ala
 1               5                  10                 15

Leu Ala Lys His Leu Ala Lys Ala Leu Ala Lys Ala Leu Lys Cys Glu
            20                  25                  30

Ala
```

```
<210> SEQ ID NO 10
<211> LENGTH: 16
<212> TYPE: PRT
<213> ORGANISM: artificial sequence
<220> FEATURE:
<223> OTHER INFORMATION: synthetic sequence

<400> SEQUENCE: 10

Arg Gln Ile Lys Ile Trp Phe Gln Asn Arg Met Lys Trp Lys Lys
1               5                   10                  15

<210> SEQ ID NO 11
<211> LENGTH: 135
<212> TYPE: PRT
<213> ORGANISM: Homo sapiens

<400> SEQUENCE: 11

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
                20                  25                  30

Leu Asn Leu Gly Lys Asp Ser Asn Asn Leu Cys Leu His Phe Asn Pro
            35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135

<210> SEQ ID NO 12
<211> LENGTH: 698
<212> TYPE: PRT
<213> ORGANISM: Homo sapiens

<400> SEQUENCE: 12

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
                20                  25                  30

His Glu Ala Thr Lys Cys Gln Ser Phe Arg Asp His Met Lys Ser Val
            35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
```

-continued

```
                130                 135                 140
Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
                180                 185                 190

Cys Pro Gly Cys Gly Cys Ser Thr Leu Asn Gln Tyr Phe Gly Tyr Ser
                195                 200                 205

Gly Ala Phe Lys Cys Leu Lys Asp Gly Ala Gly Asp Val Ala Phe Val
                210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
                260                 265                 270

Arg Ser Met Gly Gly Lys Glu Asp Leu Ile Trp Glu Leu Leu Asn Gln
                275                 280                 285

Ala Gln Glu His Phe Gly Lys Asp Lys Ser Lys Glu Phe Gln Leu Phe
                290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
                340                 345                 350

Ala Pro Thr Asp Glu Cys Lys Pro Val Lys Trp Cys Ala Leu Ser His
                355                 360                 365

His Glu Arg Leu Lys Cys Asp Glu Trp Ser Val Asn Ser Val Gly Lys
                370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
                420                 425                 430

Lys Ser Asp Asn Cys Glu Asp Thr Pro Glu Ala Gly Tyr Phe Ala Val
                435                 440                 445

Ala Val Val Lys Lys Ser Ala Ser Asp Leu Thr Trp Asp Asn Leu Lys
450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
                500                 505                 510

Leu Cys Lys Leu Cys Met Gly Ser Gly Leu Asn Leu Cys Glu Pro Asn
                515                 520                 525

Asn Lys Glu Gly Tyr Tyr Gly Tyr Thr Gly Ala Phe Arg Cys Leu Val
                530                 535                 540

Glu Lys Gly Asp Val Ala Phe Val Lys His Gln Thr Val Pro Gln Asn
545                 550                 555                 560
```

```
Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
        595                 600                 605

Arg Lys Asp Lys Glu Ala Cys Val His Lys Ile Leu Arg Gln Gln Gln
    610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
        675                 680                 685

Leu Leu Glu Ala Cys Thr Phe Arg Arg Pro
    690                 695
```

<210> SEQ ID NO 13
<211> LENGTH: 110
<212> TYPE: PRT
<213> ORGANISM: Homo sapiens

<400> SEQUENCE: 13

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

<210> SEQ ID NO 14
<211> LENGTH: 1954
<212> TYPE: PRT
<213> ORGANISM: Arabidopsis thaliana

<400> SEQUENCE: 14

```
Met Lys Ser Ser His Glu Val Thr Lys Asn His Ser Gly Ser Pro Ser
1               5                   10                  15

Gly Lys Lys Ser Lys Lys Leu Ala Ala Ile Cys Glu Glu Tyr Lys
                20                  25                  30

Lys Asn His Gly Glu Ser Gln Asp Arg Asp Gly Gly Ser Gly Leu Ala
            35                  40                  45

Cys Ala Asp Ser Glu Leu Arg Ser Ser Arg Val Arg Lys Ile Pro
        50                  55                  60

Ser Ile Leu Asp Ala Ser Pro Pro Pro Lys Lys Arg Gln Arg Phe
65                  70                  75                  80

Asn Lys Ser Ser Ser Ser Ile Glu Lys Gly Lys Arg Asn Glu Asp Gly
```

-continued

```
                85                  90                  95
Asp Ser Asp Ala Pro Asp Gly Trp Lys Ser Arg Leu Arg Ser Arg Arg
            100                 105                 110

Lys Lys Asn Val Gly Phe Gln Ala Ser Gly Arg Gln Arg Arg Val Val
        115                 120                 125

Lys Gly Lys Arg Lys Leu Val Phe Arg Asn Arg Ala Cys Glu Leu Ser
    130                 135                 140

Glu Lys Ala Glu Ala Ser Asp Arg Glu Glu Lys Gly Ala Leu Lys
145                 150                 155                 160

Gly Gly Lys Leu Asn Lys Ala Lys Lys Pro Val Asp Val Lys Glu Ser
            165                 170                 175

Glu Ser Ser Glu Asp Gly Lys Ser Asp Thr Ser Asn Ser Glu
        180                 185                 190

Asp Val Gln Lys Glu Ser Asp Thr Ser Asn Ser Glu Asp Ser Ala
    195                 200                 205

Ser Glu Ser Glu Glu Ser Met Gln Ala Asp Ser Ala Ala Arg Glu Lys
210                 215                 220

Tyr Gln Glu Lys Lys Ala Thr Lys Arg Ser Val Phe Leu Glu Ser Glu
225                 230                 235                 240

Asn Glu Ala Glu Val Asp Arg Thr Glu Thr Glu Ser Glu Asp Gly Thr
            245                 250                 255

Asp Ser Thr Asp Asn Glu Ile Asp Asp Ser Asp Glu Gly Glu Ser
        260                 265                 270

Glu Thr Gln Cys Ser Ala Glu Lys Thr Gly Ser Glu Thr Glu Ala Asn
    275                 280                 285

Val Glu Glu Met Arg Ala Asp Thr Asn Val Thr Met Glu Ala Val Gln
290                 295                 300

Asn Glu Ser Arg Asn Gln Met Glu Glu Leu Glu Asn Glu Ile Glu Met
305                 310                 315                 320

Gly Val Glu Asp Glu Lys Lys Glu Met Ser Val Ile Val Ser Glu Ser
            325                 330                 335

Gly Asn Gly Thr Gly Ile Arg Glu Asp Glu Asn Lys Glu Met Asp Val
        340                 345                 350

Ile Val Ser Glu Ser Gly Asn Gly Thr Gly Ile Leu Glu Gly Glu Asn
    355                 360                 365

Lys Lys Met Glu Val Met Val Ser Gly Ser Gly Asn Gly Thr Gly Ile
370                 375                 380

Arg Glu Asp Asp Ser Asp Phe Ala Ala Lys Val Lys Asn Arg Glu Gly
385                 390                 395                 400

Asp Thr Leu His Pro Glu Leu Leu Gly Glu Ala Ser Thr Glu Ile Asn
            405                 410                 415

Glu Ser Leu Lys Gln Asn Asp Asp Ile Gly Glu Gln Gly Val Ser Arg
        420                 425                 430

Thr Pro Ser Asn Asn Lys Thr Lys Glu His Asn Glu Phe Leu Asp Arg
    435                 440                 445

Gly Gly Glu Ser Val Glu Met Pro Asp Glu Leu Pro Ile Gln Asn Glu
450                 455                 460

Thr Cys Lys Lys Ala Val Asp Ser Val Ser Thr Ser Ser Asp Arg Leu
465                 470                 475                 480

Gly Lys Pro Leu Phe Lys Gln Thr Arg Arg Cys Gly Leu Cys Gly Val
            485                 490                 495

Gly Thr Asp Gly Lys Leu Pro Lys Lys Leu Met Gln Asn Gly Asp
        500                 505                 510
```

```
Ser Asp Val Glu Ala Pro Ser Gly Ser Ser Ser Glu Glu Gln Lys
        515                 520                 525

Tyr Asp Ile Leu Asp Gly Phe Gly Asp Pro Gly Trp Leu Gly Arg
        530                 535                 540

Leu Leu Gly Pro Ile Asn Asp Arg Tyr Gly Ile Ser Gly Thr Trp Val
545                 550                 555                 560

His Gln Asn Cys Ala Val Trp Ser Pro Glu Val Tyr Phe Ala Gly Val
            565                 570                 575

Gly Cys Leu Lys Asn Ile Arg Ala Ala Leu Phe Arg Gly Arg Ser Leu
                580                 585                 590

Lys Cys Thr Arg Cys Asp Arg Pro Gly Ala Thr Thr Gly Cys Arg Pro
        595                 600                 605

Cys Ala Arg Ala Asn Gly Cys Ile Phe Asp His Arg Lys Phe Leu Ile
    610                 615                 620

Ala Cys Thr Asp His Arg His His Phe Gln Pro His Gly Arg Gln Cys
625                 630                 635                 640

Gln Val Arg Met Thr Lys Met Lys Thr Lys Arg Met Arg Leu Glu Met
                    645                 650                 655

Lys Lys His Ser Asn Asp Ala Trp Arg Lys Asp Val Glu Ala Glu Glu
                660                 665                 670

Lys Trp Phe Glu Lys Cys Gly Glu Asp Glu Phe Leu Lys Arg Glu
            675                 680                 685

Ser Lys Arg Leu His Arg Asp Leu Leu Arg Val Ala Pro Glu Tyr Ile
    690                 695                 700

Gly Gly Ser Asp Ser Glu Ser Gly Lys Ala Phe Glu Gly Trp Asp Ser
705                 710                 715                 720

Val Ala Gly Leu Glu Gly Val Thr Gln Cys Met Lys Glu Val Val Leu
                    725                 730                 735

Ile Pro Leu Leu Tyr Pro Glu Phe Phe Asp Asn Leu Gly Leu Thr Pro
                740                 745                 750

Pro Arg Gly Ile Leu His Gly His Pro Gly Thr Gly Lys Thr Leu
        755                 760                 765

Val Val Arg Ala Leu Ile Gly Ser Leu Ala Arg Gly Asn Arg Arg Ile
    770                 775                 780

Ala Tyr Phe Ala Arg Lys Gly Ala Asp Cys Leu Gly Lys Tyr Val Gly
785                 790                 795                 800

Asp Ala Glu Arg Gln Leu Arg Leu Leu Phe Gln Val Ala Glu Lys Cys
                    805                 810                 815

Gln Pro Ser Ile Ile Phe Phe Asp Glu Ile Asp Gly Leu Ala Pro Lys
            820                 825                 830

Arg Ser Arg Gln Gln Asp Gln Thr His Ser Ser Val Val Ser Thr Leu
                835                 840                 845

Leu Ala Leu Leu Asp Gly Leu Lys Ser Arg Gly Ser Val Val Ile
850                 855                 860

Gly Ala Thr Asn Tyr Pro Asp Ala Ile Asp Pro Ala Leu Arg Arg Pro
865                 870                 875                 880

Gly Arg Phe Asp Arg Glu Ile Tyr Phe Pro Leu Pro Ser Val Asp Asp
            885                 890                 895

Arg Ala Ala Ile Ile Ser Leu His Thr Arg Lys Trp Pro Lys Pro Val
                900                 905                 910

Ser Gly Tyr Leu Leu Lys Trp Ile Ala Lys Glu Thr Ala Gly Phe Ala
            915                 920                 925

Gly Ala Asp Ile Gln Ala Leu Cys Thr Gln Ala Ala Met Ile Ala Leu
930                 935                 940
```

```
Asn Arg Ser Phe Pro Leu Gln Glu Ser Leu Ala Ala Ala Glu Leu Gly
945                 950                 955                 960

Val Ser Ser Ser Asn Arg Ala Ala Leu Pro Ser Phe Ser Val Glu Glu
                965                 970                 975

Arg Asp Trp Leu Glu Ala Leu Ser Arg Ser Pro Pro Pro Cys Ser Arg
            980                 985                 990

Arg Gly Ala Gly Ile Ala Ala Ser Asp Ile Phe Ser Ser Pro Leu Pro
        995                 1000                1005

Thr Tyr Leu Val Pro Ser Leu Leu Pro Pro Leu Cys Ser Leu Leu
    1010                1015                1020

Val Ala Leu His Leu Asp Glu Arg Ile Phe Leu Pro Pro Leu Leu
    1025                1030                1035

Ser Lys Ala Ala Val Asp Val Gln Asn Val Ile Arg Ser Ala Leu
    1040                1045                1050

Ser Asp Lys Lys Ile Thr Glu Gly Cys Trp Trp Ser His Val Asp
    1055                1060                1065

Thr Leu Leu His Glu Val Asp Val Val Lys Asp Ile Val Gln Arg
    1070                1075                1080

Leu Ser Cys Thr Gly Ile Leu Asp Gly Gly Cys Asp Leu Val Gly
    1085                1090                1095

Ser Val Ala Ser Ile Pro Gly Thr Gly Asp Cys Ser Leu Gly Ser
    1100                1105                1110

Ala Lys Phe Met Val Pro Arg Val Cys Arg His Pro Gly Val Leu
    1115                1120                1125

Gly Asn Ala Ser Val Glu Ser Thr Ser Lys Ser Gly Phe Gln Leu
    1130                1135                1140

Leu Ile Ala Gly Gly Pro Lys Ser Gly Gln Arg His Leu Ala Ser
    1145                1150                1155

Cys Val Leu His Cys Phe Ile Gly Asn Ala Glu Met Leu Lys Ile
    1160                1165                1170

Asp Thr Ala Thr Ile Ser Gln Glu Gly Asn Gly Asp Leu Val Leu
    1175                1180                1185

Gly Val Thr His Leu Leu Ile Lys Cys Ala Ser Lys Lys Ser Cys
    1190                1195                1200

Val Val Phe Met Pro Arg Val Asp Leu Trp Ala Val Lys Thr Glu
    1205                1210                1215

Thr Pro Leu Asn Glu Glu Val Glu Cys Asp Asp Ser Val Gln
    1220                1225                1230

Glu Asn Cys Ser Glu Met Gly Glu Glu Lys Ala Leu Gln Asn Gly
    1235                1240                1245

Val Arg Val Ser His Ala Trp Asn Thr Phe Phe Glu Gln Val Glu
    1250                1255                1260

Thr Leu Arg Val Ser Thr Lys Met Met Ile Leu Ala Thr Ser Gly
    1265                1270                1275

Met Pro Tyr Lys Leu Leu Pro Pro Lys Ile Gln Gln Phe Phe Lys
    1280                1285                1290

Thr Asp Leu Ser Lys Glu Cys Gln Pro Thr Met Ser Glu Ala Val
    1295                1300                1305

Pro Gln Phe Asn Val Gln Val Glu Ser Ser Asp Gln Asp Ile
    1310                1315                1320

Ala Ile Asp Leu Ser Ala Thr Glu Leu Leu Arg Arg Ala Ile Gln
    1325                1330                1335

Val Phe Leu His Leu Val His Gln Gly Ser His Thr His Cys Gly
```

-continued

```
              1340            1345            1350

Leu Lys Lys Lys Tyr Lys Gly Glu Asp Leu Asp Gln Gly Cys Arg
    1355            1360            1365

Asp Ala Ala Pro Gln Asn Asn Thr Asp His Arg Ala Gly Glu Glu
    1370            1375            1380

Ala Val Val Lys Ser Lys Arg Leu Asp Asp Gly Ser Leu Lys Val
    1385            1390            1395

Pro Pro Leu Pro Ile Asn Ile Asn Val Lys Pro Lys Ser Ser Leu
    1400            1405            1410

Gln Leu Ala Val Ser Thr Phe Gly Tyr Gln Ile Leu Gln Tyr Pro
    1415            1420            1425

Gln Phe Ala Glu Leu Cys Trp Val Thr Ser Lys Leu Lys Glu Gly
    1430            1435            1440

Pro Ser Ala Asp Val Ser Gly Pro Trp Arg Gly Trp Pro Phe Asn
    1445            1450            1455

Ser Cys Ile Thr Arg Pro Cys Asn Ser Ser Glu Gln Thr Ile Thr
    1460            1465            1470

Ser Ser Asp Ser Asn Asn Val Lys Gly Lys Asp Ser Thr Gly Ile
    1475            1480            1485

Val Arg Gly Leu Thr Ala Val Gly Leu Ser Ala Tyr Arg Gly Thr
    1490            1495            1500

Tyr Ile Ser Leu Arg Glu Val Ser Phe Glu Val Arg Lys Val Leu
    1505            1510            1515

Glu Leu Leu Val Gly Arg Ile Ser Val Lys Ile Asn Ala Gly Lys
    1520            1525            1530

Asp Arg Cys Arg Tyr Ile Arg Ile Leu Ser Gln Val Ala Tyr Leu
    1535            1540            1545

Glu Asp Leu Val Asn Ser Trp Val Tyr Ala Met Arg Ser Phe Glu
    1550            1555            1560

Ser Thr Thr Gln Thr Glu Ser Thr Asn Pro Leu Pro Cys Ser Val
    1565            1570            1575

Val Asn Pro Ser Val Arg Asn Glu Pro Thr Glu Gln Gly Thr Ser
    1580            1585            1590

Asp Gln Leu Lys Gly Ser Glu Glu Asp Leu Lys Glu Asp Thr Gln
    1595            1600            1605

Asn Met Asn Cys Pro Asp Pro Ile Ala Ser Ser Asn Leu Thr Asp
    1610            1615            1620

Asn His Gln Pro Val Val Glu Ile Ala Asn Gly His Asn Gly Thr
    1625            1630            1635

Asn His Glu Ser Phe Leu Glu Asp Thr Gly His Leu Thr Thr His
    1640            1645            1650

Ser Thr Asp Gly Leu Thr Leu Val Lys Glu Asn Val Asp Val Ile
    1655            1660            1665

Ser Asp Thr Glu Met Met Ile Glu Asp Ser Gly Val Asn Pro Phe
    1670            1675            1680

Arg Gln Ala Val Leu Leu Asp Leu Asn Ser Pro Ala Ala Asp His
    1685            1690            1695

Glu Gln Asn Glu Thr Pro His Gly Ser Cys Glu Val Glu Thr Thr
    1700            1705            1710

Gly Thr Val Ile Ser Leu Gln Glu Lys Ala Asp Ser Leu Asp Asn
    1715            1720            1725

Pro Asn Gly Ser Gly Asp Ser Asn Ser Ile Ser Leu Glu Asp Pro
    1730            1735            1740
```

-continued

```
His Lys Ser Ala Asp Ser Asn Asn Gly Lys Ala Trp Asp Gly Val
    1745                1750                1755
His Gly Leu Glu Ser Ala Asn Asn Met Pro Glu Pro Val Glu Gln
    1760                1765                1770
Val Glu Thr Thr Gly Arg Thr Asn Pro Gln Asp Pro Ser Leu
    1775                1780                1785
Val Cys Leu Tyr Arg Cys Cys Ser Gln Cys Val Ser Ile Leu Gln
    1790                1795                1800
Asp Ser Met His Lys Leu Val Thr Arg Glu Leu Arg Leu Gly Arg
    1805                1810                1815
Ser Ser Ile Thr Thr Glu Gly Ile His Asp Ala Val Ser Ser Leu
    1820                1825                1830
Ser Val Glu Leu Ile Ser Ala Val Arg Lys Phe Ile Ser Val Lys
    1835                1840                1845
Asn Asn Gly Thr Met Gln Glu Ala Lys Val Lys Asp His Glu Glu
    1850                1855                1860
Cys Pro Glu Asn Glu Ala Cys Phe Cys Lys Arg Leu Ser Gly Asn
    1865                1870                1875
Phe Leu Ala Ser Val Glu Cys Cys Ser His Ser Ala Glu Met Gln
    1880                1885                1890
Gly Ser Leu Asp Glu Gly Asn Thr Tyr Arg Arg Pro Lys Thr Trp
    1895                1900                1905
Leu Glu Pro Val Phe Val Phe Lys Asp Gly Ile Leu Val Pro Val
    1910                1915                1920
Ser Thr Glu Asp Asp Arg Ser Leu His Cys Lys Tyr Asp Ser Phe
    1925                1930                1935
Cys Leu Gly Ser Leu Ile Glu Leu Ile Ala Thr Glu Met Lys Pro
    1940                1945                1950
Phe

<210> SEQ ID NO 15
<211> LENGTH: 29
<212> TYPE: PRT
<213> ORGANISM: Homo sapiens

<400> SEQUENCE: 15

Met Arg Pro Ser Gly Thr Ala Gly Ala Ala Leu Leu Ala Leu Leu Ala
1               5                   10                  15
Ala Leu Cys Pro Ala Ser Arg Ala Leu Glu Glu Lys Lys
                20                  25

<210> SEQ ID NO 16
<211> LENGTH: 160
<212> TYPE: PRT
<213> ORGANISM: Homo sapiens

<400> SEQUENCE: 16

Met Val Pro Ser Ala Gly Gln Leu Ala Leu Phe Ala Leu Gly Ile Val
1               5                   10                  15
Leu Ala Ala Cys Gln Ala Leu Glu Asn Ser Thr Ser Pro Leu Ser Ala
                20                  25                  30
Asp Pro Pro Val Ala Ala Val Val Ser His Phe Asn Asp Cys Pro
            35                  40                  45
Asp Ser His Thr Gln Phe Cys Phe His Gly Thr Cys Arg Phe Leu Val
        50                  55                  60
Gln Glu Asp Lys Pro Ala Cys Val Cys His Ser Gly Tyr Val Gly Ala
65                  70                  75                  80
```

-continued

Arg Cys Glu His Ala Asp Leu Leu Ala Val Val Ala Ala Ser Gln Lys
                85                  90                  95

Lys Gln Ala Ile Thr Ala Leu Val Val Val Ser Ile Val Ala Leu Ala
            100                 105                 110

Val Leu Ile Ile Thr Cys Val Leu Ile His Cys Cys Gln Val Arg Lys
            115                 120                 125

His Cys Glu Trp Cys Arg Ala Leu Ile Cys Arg His Glu Lys Pro Ser
130                 135                 140

Ala Leu Leu Lys Gly Arg Thr Ala Cys Cys His Ser Glu Thr Val Val
145                 150                 155                 160

<210> SEQ ID NO 17
<211> LENGTH: 331
<212> TYPE: PRT
<213> ORGANISM: artificial sequence
<220> FEATURE:
<223> OTHER INFORMATION: synthetic vector

<400> SEQUENCE: 17

Met Arg Arg Arg Arg Arg Arg Arg Arg Arg Gly Glu Gly Asp
1               5                   10                  15

Ile Met Gly Glu Trp Gly Asn Glu Ile Phe Gly Ala Ile Ala Gly Phe
            20                  25                  30

Leu Gly Gly Glu His Asp Glu Ala Gln Gln Asn Ala Phe Tyr Gln Val
            35                  40                  45

Leu Asn Met Pro Asn Leu Asn Ala Asp Gln Arg Asn Gly Phe Ile Gln
        50                  55                  60

Ser Leu Lys Asp Asp Pro Ser Gln Ser Ala Asn Val Leu Gly Glu Ala
65                  70                  75                  80

His Asp Glu Ala Gln Gln Asn Ala Phe Tyr Gln Val Leu Asn Met Pro
                85                  90                  95

Asn Leu Asn Ala Asp Gln Arg Asn Gly Phe Ile Gln Ser Leu Lys Asp
            100                 105                 110

Asp Pro Ser Gln Ser Ala Asn Val Leu Gly Glu Ala Gly Glu Gly Ser
            115                 120                 125

Ser Val Leu Ala Ser Cys Pro Lys Lys Pro Val Ser Ser Tyr Leu Arg
130                 135                 140

Phe Ser Lys Glu Gln Leu Pro Ile Phe Lys Ala Gln Asn Pro Asp Ala
145                 150                 155                 160

Lys Thr Thr Glu Leu Ile Arg Arg Ile Ala Gln Arg Trp Arg Glu Leu
                165                 170                 175

Pro Asp Ser Lys Lys Lys Ile Tyr Gln Asp Ala Tyr Arg Ala Glu Trp
            180                 185                 190

Gln Val Tyr Lys Glu Glu Ile Ser Arg Phe Lys Glu Gln Leu Thr Pro
            195                 200                 205

Ser Gln Ile Met Ser Leu Glu Lys Glu Ile Met Asp Lys His Leu Lys
        210                 215                 220

Arg Lys Ala Met Thr Lys Lys Glu Leu Thr Leu Leu Gly Lys Pro
225                 230                 235                 240

Lys Arg Pro Arg Ser Ala Tyr Asn Val Tyr Val Ala Glu Arg Phe Gln
                245                 250                 255

Glu Ala Lys Gly Asp Ser Pro Gln Glu Lys Leu Lys Thr Val Lys Glu
            260                 265                 270

Asn Trp Lys Asn Leu Ser Asp Ser Glu Lys Glu Leu Tyr Ile Gln His
            275                 280                 285

```
Ala Lys Glu Asp Glu Thr Arg Tyr His Asn Glu Met Lys Ser Trp Glu
    290                 295                 300

Glu Gln Met Ile Glu Val Gly Arg Lys Asp Leu Leu Arg Arg Thr Ile
305                 310                 315                 320

Lys Lys Gln Arg Lys Tyr Gly Ala Glu Glu Cys
                325                 330

<210> SEQ ID NO 18
<211> LENGTH: 246
<212> TYPE: PRT
<213> ORGANISM: Homo sapiens

<400> SEQUENCE: 18

Met Ala Pro Leu Ala Ser Met Thr Gly Val Leu Ser Ala Leu Gly Ala
1               5                   10                  15

Ser Gly Ala Gly Leu Cys Thr Gly Cys Gly Ser Ala Leu Ala Ser Pro
            20                  25                  30

Pro Ser Pro Val Thr Leu Pro Ala Thr Pro Ser Val Leu Ala Ser
        35                  40                  45

Cys Pro Leu Leu Pro Val Ser Ser Thr Leu Ala Pro Ser Leu Gly Gly
50                  55                  60

Leu Pro Ile Pro Leu Ala Gly Ala Pro Ala Ala Leu Thr Thr Gly Leu
65                  70                  75                  80

Ile Ala Ala Ile Ala Gly Ala Thr Ala Gly Leu Pro Ala Ser Leu Leu
                85                  90                  95

Leu Ile Thr Gly Ala Ala Thr Ala Ala Gly Thr Gly Val Thr Leu Gly
            100                 105                 110

Gly Ile Ser Ala Pro Leu Gly Gly Leu Thr Pro Ser Gly Ile Met Ser
        115                 120                 125

Leu Gly Leu Gly Ile Met Ala Leu His Leu Leu Ala Leu Ala Met Thr
130                 135                 140

Leu Leu Leu Gly Leu Thr Leu Leu Gly Leu Pro Leu Ala Pro Ala Ser
145                 150                 155                 160

Ala Thr Ala Val Thr Val Ala Gly Ala Pro Gly Gly Ala Leu Gly Ala
                165                 170                 175

Ser Pro Gly Gly Leu Leu Leu Thr Val Leu Gly Ala Thr Leu Ala Leu
            180                 185                 190

Ser Ala Ser Glu Lys Glu Leu Tyr Ile Gly His Ala Leu Gly Ala Gly
        195                 200                 205

Thr Ala Thr His Ala Gly Met Leu Ser Thr Gly Gly Met Ile Gly
    210                 215                 220

Val Gly Ala Leu Ala Leu Leu Ala Ala Thr Ile Leu Leu Gly Ala Leu
225                 230                 235                 240

Thr Gly Ala Gly Gly Cys
            245

<210> SEQ ID NO 19
<211> LENGTH: 243
<212> TYPE: PRT
<213> ORGANISM: Mus musculus

<400> SEQUENCE: 19

Met Ala Leu Phe Arg Gly Met Trp Ser Val Leu Lys Ala Leu Gly Arg
1               5                   10                  15

Thr Gly Val Glu Met Cys Ala Gly Cys Gly Gly Arg Ile Pro Ser Ser
            20                  25                  30

Ile Ser Leu Val Cys Ile Pro Lys Cys Phe Ser Ser Met Gly Ser Tyr
```

```
                35                  40                  45
Pro Lys Lys Pro Met Ser Ser Tyr Leu Arg Phe Ser Thr Glu Gln Leu
 50                  55                  60

Pro Lys Phe Lys Ala Lys His Pro Asp Ala Lys Leu Ser Glu Leu Val
 65                  70                  75                  80

Arg Lys Ile Ala Ala Leu Trp Arg Glu Leu Pro Glu Ala Glu Lys Lys
                 85                  90                  95

Val Tyr Glu Ala Asp Phe Lys Ala Glu Trp Lys Ala Tyr Lys Glu Ala
                100                 105                 110

Val Ser Lys Tyr Lys Glu Gln Leu Thr Pro Ser Gln Leu Met Gly Met
            115                 120                 125

Glu Lys Glu Ala Arg Gln Arg Leu Lys Lys Ala Leu Val Lys
130                 135                 140

Arg Arg Glu Leu Ile Leu Leu Gly Lys Pro Lys Arg Pro Arg Ser Ala
145                 150                 155                 160

Tyr Asn Ile Tyr Val Ser Glu Ser Phe Gln Glu Ala Lys Asp Asp Ser
                165                 170                 175

Ala Gln Gly Lys Leu Lys Leu Val Asn Glu Ala Trp Lys Asn Leu Ser
            180                 185                 190

Pro Glu Glu Lys Gln Ala Tyr Ile Gln Leu Ala Lys Asp Asp Arg Ile
        195                 200                 205

Arg Tyr Asp Asn Glu Met Lys Ser Trp Glu Gln Met Ala Glu Val
210                 215                 220

Gly Arg Ser Asp Leu Ile Arg Arg Ser Val Lys Arg Ser Gly Asp Ile
225                 230                 235                 240

Ser Glu His

<210> SEQ ID NO 20
<211> LENGTH: 244
<212> TYPE: PRT
<213> ORGANISM: Rattus norvegicus

<400> SEQUENCE: 20

Met Ala Leu Phe Arg Gly Met Trp Gly Val Leu Arg Thr Leu Gly Arg
 1               5                  10                  15

Thr Gly Val Glu Met Cys Ala Gly Cys Gly Gly Arg Ile Pro Ser Pro
                20                  25                  30

Val Ser Leu Ile Cys Ile Pro Lys Cys Phe Ser Ser Leu Gly Asn Tyr
            35                  40                  45

Pro Lys Lys Pro Met Ser Ser Tyr Leu Arg Phe Ser Thr Glu Gln Leu
 50                  55                  60

Pro Lys Phe Lys Ala Lys His Pro Asp Ala Lys Val Ser Glu Leu Ile
 65                  70                  75                  80

Arg Lys Ile Ala Ala Met Trp Arg Glu Leu Pro Glu Ala Glu Lys Lys
                 85                  90                  95

Val Tyr Glu Ala Asp Phe Lys Ala Glu Trp Lys Val Tyr Lys Glu Ala
                100                 105                 110

Val Ser Lys Tyr Lys Glu Gln Leu Thr Pro Ser Gln Leu Met Gly Leu
            115                 120                 125

Glu Lys Glu Ala Arg Gln Lys Arg Leu Lys Lys Ala Gln Ile Lys
130                 135                 140

Arg Arg Glu Leu Ile Leu Leu Gly Lys Pro Lys Arg Pro Arg Ser Ala
145                 150                 155                 160

Tyr Asn Ile Tyr Val Ser Glu Ser Phe Gln Gly Ala Lys Asp Glu Ser
                165                 170                 175
```

-continued

Pro Gln Gly Lys Leu Lys Leu Val Asn Gln Ala Trp Lys Asn Leu Ser
                180                 185                 190

His Asp Glu Lys Gln Ala Tyr Ile Gln Leu Ala Lys Asp Asp Arg Ile
            195                 200                 205

Arg Tyr Asp Asn Glu Met Lys Ser Trp Glu Gln Met Ala Glu Val
210                 215                 220

Gly Arg Ser Asp Leu Ile Arg Arg Ser Val Lys Arg Pro Pro Gly Asp
225                 230                 235                 240

Ile Ser Glu Asn

<210> SEQ ID NO 21
<211> LENGTH: 446
<212> TYPE: PRT
<213> ORGANISM: Arabidopsis thaliana

<400> SEQUENCE: 21

Met Ser Thr Val Ser Ser Asp Pro Ala His Ala Lys Lys Ser Arg Asn
1               5                   10                  15

Ser Arg Lys Ala Leu Lys Gln Lys Asn Glu Ile Val Glu Ser Ser Pro
            20                  25                  30

Val Ser Asp Lys Gly Lys Glu Thr Lys Ser Phe Glu Lys Asp Leu Met
        35                  40                  45

Glu Met Gln Ala Met Leu Glu Lys Met Lys Ile Glu Lys Glu Lys Thr
    50                  55                  60

Glu Asp Leu Leu Lys Glu Lys Asp Glu Ile Leu Arg Lys Lys Glu Val
65                  70                  75                  80

Glu Gln Glu Lys Leu Lys Thr Glu Leu Lys Lys Leu Gln Lys Met Lys
                85                  90                  95

Glu Phe Lys Pro Asn Met Thr Phe Ala Phe Ser Gln Ser Leu Ala Gln
            100                 105                 110

Thr Glu Glu Lys Lys Gly Lys Lys Lys Lys Asp Cys Ala Glu
        115                 120                 125

Thr Lys Arg Pro Ser Thr Pro Tyr Ile Leu Trp Cys Lys Asp Asn Trp
    130                 135                 140

Asn Glu Val Lys Lys Gln Asn Pro Glu Ala Asp Phe Lys Glu Thr Ser
145                 150                 155                 160

Asn Ile Leu Gly Ala Lys Trp Lys Gly Ile Ser Ala Glu Glu Lys Lys
                165                 170                 175

Pro Tyr Glu Glu Lys Tyr Gln Ala Asp Lys Glu Ala Tyr Leu Gln Val
            180                 185                 190

Ile Thr Lys Glu Lys Arg Glu Arg Glu Ala Met Lys Leu Leu Asp Asp
        195                 200                 205

Glu Gln Lys Gln Lys Thr Ala Met Glu Leu Leu Asp Gln Tyr Leu His
    210                 215                 220

Phe Val Gln Glu Ala Glu His Asp Asn Lys Lys Ala Lys Lys Ile
225                 230                 235                 240

Lys Asp Pro Leu Lys Pro Lys Gln Pro Ile Ser Ala Tyr Leu Ile Tyr
                245                 250                 255

Ala Asn Glu Arg Arg Ala Ala Leu Lys Gly Glu Asn Lys Ser Val Ile
            260                 265                 270

Glu Val Ala Lys Met Ala Gly Glu Trp Lys Asn Leu Ser Glu Glu
        275                 280                 285

Lys Lys Ala Pro Tyr Asp Gln Met Ala Lys Lys Asn Lys Glu Ile Tyr
    290                 295                 300

Leu Gln Glu Met Glu Gly Tyr Lys Arg Thr Lys Glu Glu Ala Met
305                 310                 315                 320

Ser Gln Lys Lys Glu Glu Glu Phe Met Lys Leu His Lys Gln Glu
            325                 330                 335

Ala Leu Gln Leu Leu Lys Lys Lys Glu Lys Thr Asp Asn Ile Ile Lys
            340                 345                 350

Lys Thr Lys Glu Thr Ala Lys Asn Lys Lys Asn Glu Asn Val Asp
            355                 360                 365

Pro Asn Lys Pro Lys Pro Thr Ser Ser Tyr Phe Leu Phe Cys Lys
370                 375                 380

Asp Ala Arg Lys Ser Val Leu Glu Glu His Pro Gly Ile Asn Asn Ser
385                 390                 395                 400

Thr Val Thr Ala His Ile Ser Leu Lys Trp Met Glu Leu Gly Glu Glu
            405                 410                 415

Glu Lys Gln Val Tyr Asn Ser Lys Ala Ala Glu Leu Met Glu Ala Tyr
            420                 425                 430

Lys Lys Glu Val Glu Glu Tyr Asn Lys Thr Lys Thr Ser Ser
            435                 440                 445

<210> SEQ ID NO 22
<211> LENGTH: 204
<212> TYPE: PRT
<213> ORGANISM: Caenorhabditis elegans

<400> SEQUENCE: 22

Met Leu Gly Thr Ile Ser Met Arg Phe Phe Ala Thr Lys Val Val Ala
1               5                   10                  15

Pro Arg Ala Ser Val Ala Ala Ser Thr Pro Gln Val Pro Leu Gly Met
            20                  25                  30

Asn Ile Asn Pro Tyr Ala Met Phe Ile Lys Glu Asn Phe Lys Ala Asn
        35                  40                  45

Thr Ser Asp Met Lys Arg Thr Asp Leu Met Lys Glu Leu Ser Gly Lys
    50                  55                  60

Trp Lys Ala Leu Ser Ile Ser Glu Lys Asp Lys Tyr Thr Glu Leu Ser
65                  70                  75                  80

Lys Asn Tyr Asn Ala Gln Lys Leu Asp Asp Phe Met Lys Leu Ser Thr
                85                  90                  95

Glu Glu Gln Lys Lys Leu Val Asp Ser Ala Lys Glu Lys Lys Ala Glu
            100                 105                 110

Arg Ala Ser Arg Arg His Ala Lys Glu Arg Arg Glu Lys Arg Lys Gln
        115                 120                 125

Ser Gly Arg Pro Ser Val Pro Pro Ser Ala Tyr Ala Leu Phe Ile Lys
    130                 135                 140

Glu Lys Leu Ser Gly Ala Gly Met Glu Ser Lys Glu Lys Met Lys Glu
145                 150                 155                 160

Ala Val Ala Gln Trp Lys Ala Phe Thr Asp Ser Gln Lys Lys Lys Tyr
                165                 170                 175

Thr Asp Glu Ala Lys Lys Leu Lys Asp Glu Tyr His Val Val Leu Gln
            180                 185                 190

Lys Trp Glu Ala Glu Gln Lys Glu Asn Ala Asp Gln
        195                 200

<210> SEQ ID NO 23
<211> LENGTH: 257
<212> TYPE: PRT
<213> ORGANISM: Drosophila melanogaster -continued

```
<400> SEQUENCE: 23

Met Ile Tyr Thr Thr Thr Leu Met Ser Ser Arg Gly Gly Leu Ile Gly
1               5                   10                  15

Ser Leu Ile Asn Lys Val Arg Pro Leu Ala Ala Ala Ser Ile Ser Asn
            20                  25                  30

Thr Pro Ala Val Pro Ser Lys Thr Leu Glu Glu Gln Leu Gly Leu Pro
        35                  40                  45

Pro Arg Pro Lys Lys Pro Leu Thr Pro Tyr Phe Arg Phe Met Arg Glu
    50                  55                  60

Gln Arg Pro Lys Leu Lys Ala Ala Asn Pro Gln Ile Thr Thr Val Glu
65                  70                  75                  80

Val Val Arg Gln Leu Ser Lys Asn Trp Ser Asp Ala Asp Ala Gln Leu
                85                  90                  95

Lys Glu Arg Leu Gln Ala Glu Phe Lys Arg Asp Gln Gln Ile Tyr Val
            100                 105                 110

Glu Glu Arg Thr Lys Tyr Asp Ala Thr Leu Thr Glu Glu Gln Arg Ala
            115                 120                 125

Glu Ile Lys Gln Leu Lys Gln Asp Leu Val Asp Ala Lys Glu Arg Arg
        130                 135                 140

Gln Leu Arg Lys Arg Val Lys Glu Leu Gly Arg Pro Lys Lys Pro Ala
145                 150                 155                 160

Ser Ala Phe Leu Arg Phe Ile Ala Ser Glu Arg Ile Asn Thr Pro Gln
                165                 170                 175

Gly Asp Lys Gln Thr Tyr Arg Glu Trp His Gln Lys Thr Thr Ala Lys
            180                 185                 190

Trp Thr Arg Leu Ser Asp Ser Glu Lys Glu Val Tyr Met Gln Glu Ser
            195                 200                 205

Arg Lys Glu Met Glu Leu Tyr Arg Lys Ala Ile Ser Val Trp Glu Glu
        210                 215                 220

Lys Met Ile Arg Leu Gly His Ile Asp Val Val Arg His Gly Asn Leu
225                 230                 235                 240

Ile Asp Pro Pro Glu Pro Lys Pro Arg Lys Thr Leu Ala Ser Lys Asp
                245                 250                 255

Ile
```

NONVIRAL VECTORS FOR DELIVERING POLYNUCLEOTIDES TO TARGET TISSUES

CROSS-REFERENCE TO RELATED APPLICATIONS

This application is a continuation-in-part application of U.S. patent application Ser. No. 10/972,963 filed on Oct. 25, 2004, now U.S. Pat. No. 8,039,587, which claims priority to U.S. Provisional Application No. 60/568,436 filed on May 5, 2004, and U.S. Provisional Application No. 60/513,983 filed on Oct. 24, 2003, and where permissible each of which is incorporated by reference in their entirety.

STATEMENT REGARDING FEDERALLY SPONSORED RESEARCH OR DEVELOPMENT

Aspects of the following disclosure were supported in part by NIH-NIA SBIR grant number AG022780. Therefore, the United States has certain rights in the disclosure.

FIELD OF THE INVENTION

The present disclosure is generally directed to compositions and methods for the delivery of polynucleotides, more particularly to compositions and methods for transfection, for example transfection of cells in a cell type specific manner.

BACKGROUND OF THE INVENTION

In the course of evolution, many organisms tackled the task of introducing macromolecules into living cells. Aside from the cell-specific, usually receptor-mediated or active uptake mechanisms, the general solution that has independently emerged in many lineages relies on peptides specifically evolved to interact with, and insert into lipid bilayer membranes. Thus, bacterial colicins, human porins, and protein transduction domains (PTDs) from diverse species share the motif of a positively charged alpha-helix, frequently with an amphipathic structure, which is capable of inserting into lipid membranes, and delivering larger cargoes intracellularly. Recent research reports confirm the successful use of PTDs fused to proteins for their delivery across biological boundaries, including the blood-brain barrier, and the placenta.

Another issue of great importance in the delivery of macromolecules in organisms is the need to protect them from proteolytic, nucleolytic and immune degradation and removal while traversing extracellular spaces. An often used approach is coating DNA with proteins capable of surviving the harsh journey to the target. Viral capsid proteins have been quite successful, yet for the purpose of DNA delivery in humans they suffer from a significant drawback—immunogenicity, the capacity to evoke a strong immune reaction greatly reducing the effectiveness of gene therapy.

Furthermore, it is desirable to deliver genes to specific cell and tissue types. Though expression of genes can be controlled by the selection of tissue and cell specific promoters, vector tropism is preferred. Thus, there is a need for improved compositions and methods for the delivery of polynucleotides to specific tissue and cell types.

SUMMARY OF THE INVENTION

Non-viral polynucleotide delivery vehicles and methods of their use are provided. In general, the disclosure provides modified polynucleotide-binding proteins comprising a targeting signal, for example a cell specific targeting signal. One aspect provides a polypeptide comprising at least one HMG box domain, more typically at least two HMG box domains and optionally at least targeting signal. The polypeptide can associate with a polynucleotide causing the polynucleotide to condense. The polypeptide can also coat the polynucleotide. Coating and/or condensing the polynucleotide helps protect the polynucleotide from degradation. The targeting signal helps direct the complex to a site of interest and thereby deliver the polynucleotide.

The disclosed compositions can be used to deliver polynucleotides to specific cells. In some aspects, the polynucleotides encode a protein with therapeutic utility or consist of inhibitory RNA. Accordingly, some aspects provide methods for gene therapy.

DETAILED DESCRIPTION OF THE INVENTION

1. Definitions

In describing and claiming the disclosed subject matter, the following terminology will be used in accordance with the definitions set forth below.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (H is, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" and "similarity" can be readily calculated by known methods, including, but not limited to, those described in (Computational Molecular Biology, Lesk A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H G., Eds., Humana Press, New Jersey, 1994; Sequence Analysis in Molecular Biology, von Heinje, G., Academic Press, 1987; and Sequence Analysis Primer, Gribskov, M and Devereux, J., Eds, M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "low stringency" refers to conditions that permit a polynucleotide or polypeptide to bind to another substance with little or no sequence specificity.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "treating" includes alleviating the symptoms associated with a specific disorder or condition and/or preventing or eliminating said symptoms.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

"Localization Signal or Sequence or Domain" or "Targeting Signal or Sequence or Domain" are used interchangeably and refer to a signal that directs a molecule to a specific cell, tissue, organelle, intracellular region or cell state. The signal can be polynucleotide, polypeptide, or carbohydrate moiety or can be an organic or inorganic compound sufficient to direct an attached molecule to a desired location. Exemplary targeting signals include cell targeting signals known in the art such as those provided in Table 1 and described in Wagner et al., *Targeting of Polyplexes: Toward Synthetic Virus Vector Systems* (*Adv in Gen,* 53:2005, 333-354) the disclosures of which are incorporated herein by reference in their entirety. It will be appreciated that the entire sequence listed in Table 1 need not be included, and modifications including truncations of these sequences are within the scope of the disclosure provided the sequences operate to direct a linked molecule to a specific cell type. Targeting signals of the present disclosure can have 80 to 100% identity to the sequences in Table 1. One class of suitable targeting signals include those that do not interact with the targeted cell in a receptor:ligand mechanism. For example, targeting signals include signals having or conferring a net charge, for example a positive charge. Positively charged signals can be used to target negatively charged cell types such as neurons and muscle. Negatively charged signals can be used to target positively charged cells.

"Tropism" refers to the propensity of a molecule to be attracted to a specific cell, cell type or cell state. In the art, tropism can refer to the way in which different viruses and pathogens have evolved to preferentially target to specific host species, or specific cell types within those species. The propensity for a molecule to be attracted to a specific cell, cell type or cell state can be accomplished by means of a targeting signal.

"Cell Type" is a manner of grouping or classifying cells in the art. The term cell type refers to the grouping of cells based on their biological character determined in part through common biological function, location, morphology, structure, expression of polypeptides, nucleotides or metabolites.

"Cell State" refers to the condition of a cell type. Cells are dynamic throughout their life and can achieve various states of differentiation, function, morphology and structure. As used herein, cell state refers to a specific cell type throughout its lifetime.

As used herein, the term "cell surface marker" refers to any molecule such as moiety, peptide, protein, carbohydrate, nucleic acid, antibody, antigen, and/or metabolite presented on the surface or in the vicinity of a cell sufficient to identify the cell as unique in either type or state.

"Protein Transduction Domain" or PTD refers to a polypeptide, polynucleotide, carbohydrate, or organic or inorganic compounds that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. Exemplary PTDs include but are not limited to HIV TAT YGRKKRRQRRR (SEQ. ID NO. 1) or RKKRRQRRR (SEQ. ID NO. 2); 11 Arginine residues, or positively charged polypeptides or polynucleotides having 8-15 residues, preferably 9-11 residues.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins or the nucleic acid may be incorporated into a vector.

As used herein, the term "vector" is used in reference to a vehicle used to introduce a nucleic acid sequence into a cell. A viral vector is virus that has been modified to allow recombinant DNA sequences to be introduced into host cells or cell organelles.

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term "nucleic acid" or "nucleic acid sequence" also encompasses a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

"Oligonucleotide(s)" refers to relatively short polynucleotides. Often the term refers to single-stranded deoxyribonucleotides, but it can refer as well to single- or double-stranded ribonucleotides, RNA:DNA hybrids and double-stranded DNAs, among others.

2. Modified Polynucleotide Binding or Polynucleotide-Packaging Polypeptides

A. Polynucleotide Binding Domain

The compositions and methods for the delivery of cargo, for example a polynucleotide, provided herein include polynucleotide-binding polypeptides or polynucleotide-packaging polypeptides optionally having a PTD and optionally having a targeting signal or domain. The modified or recombinant polypeptide can be any polypeptide known to bind or package a polynucleotide or a variant thereof. The recombinant polypeptide can be used as a therapeutic agent either alone or in combination with a polynucleotide. In one embodiment, the polynucleotide-binding polypeptide includes at least a portion of a member of the high mobility group (HMG) of proteins, in particular at least one HMG box domain. Generally, the HMG domain includes a global fold of three helices stabilized in an 'L-shaped' configuration by two hydrophobic cores. The high mobility group chromosomal proteins HMG1 or HMG2, which are common to all eukaryotes, bind DNA in a non-sequence-specific fashion, for example to promote chromatin function and gene regulation. They can interact directly with nucleosomes and are believed to be modulators of chromatin structure. They are also important in activating a number of regulators of gene expression, including p53, Hox transcription factors and steroid hormone receptors, by increasing their affinity for DNA. HMO proteins include HMG-1/2, HMG-I(Y) and HMG-14/17.

The HMG-1/2-box proteins can be further distinguished into three subfamilies according to the number of HMG domains present in the protein, their specific of sequence recognition and their evolutionary relationship. The first group contains chromosomal proteins bound to DNA with no sequence specificity (class I, HMG1 and HMG2), the second contains ribosomal and mitochondrial transcription factors which show sequence specificity in the presence of another associating factor when bound with DNA (class II, yeast ARS binding protein ABF-2, UBF and mitochondrial transcription factor mtTF-1), and the third contains gene-specific transcription factors which show sequence specific DNA binding (class III, lymphoid enhancer-binding factors LEF-1 and TCF-1; the mammalian sex-determining factor SRY, and the closely related SOX proteins; and the fungal regulatory proteins Mat-MC, Mat-a1, Ste1 1 and Rox1). The HMG1/2-box DNA binding domain is about 75 to about 80 amino acids and contains highly conserved proline, aromatic and basic residues. Common properties of HMG domain proteins include interaction with the minor groove of the DNA helix, binding to irregular DNA structure, and the capacity to modulate DNA structure by bending.

SOX (SRY-type HMG box) proteins have critical functions in a number of developmental processes, including sex determination, skeleton formation, pre-B and T cell development and neural induction. SOX9 plays a direct role during chondrogenesis by binding and activating the chondrocyte-specific enhancer of the Col2a1 gene. Loss of SOX9 gene function leads to the genetic condition known as Campomelic Dysplsia (CD), a form of dwarfism characterized by extreme skeletal malformation, and one in which three-quarters of XY individual are either intersexes or exhibit male to female sex reversal. There are more than 20 members cloned in SOX family. All of which contain an HMG domain, which can bind specifically to the double strand DNA motif and shares >50% identify with the HMG domain of SRY, the human testis-determining factor. The preferred DNA-binding site of SOX9 have been defined to be AGAACAATGG, which contains the SOX core-binding element (SCBE), AACAAT, flanking 5' AG and 3' GG nucleotides enhance binding by SOX9.

In one embodiment, the recombinant polynucleotide-binding protein has at least one HMG box domain, generally at least two, more particularly 2-5 HMG box domains. The HMG box domain can bind to an AT rich DNA sequence, for example, using a large surface on the concave face of the protein, to bind the minor groove of the DNA. This binding bends the DNA helix axis away from the site of contact. The first and second helices contact the DNA, their N-termini fitting into the minor groove whereas helix 3 is primarily exposed to solvent. Partial intercalation of aliphatic and aromatic residues in helix 2 occurs in the minor groove.

In other embodiments, the polynucleotide binding polypeptide can have at least one polynucleotide binding domain, typically two or more polynucleotide binding domains. The polynucleotide binding domains can be the same or different. For example, the polynucleotide-binding polypeptide can include at least on HMG box in combination with one or more DNA binding domains selected from the group consisting of an HMG box, homeodomain and POU domain; zinc finger domain such as $C_2H_2$ and $C_2C_2$; amphipathic helix domain such as leucine zipper and helix-loop-helix domains; and histone folds. The polynucleotide binding domain can be specific for a specific polynucleotide sequence, or preferably non-specifically binds to a polynucleotide. Alternatively, the polynucleotide-binding polypeptide can have more a combination of at least one polynucleotide binding domain that binds in a sequence specific manner and at least one polynucleotide binding-domain that binds DNA non-specifically.

Certain embodiments provide modified polynucleotide-binding polypeptides having a helix-turn-helix motif or at least a polynucleotide binding region of a helix-turn-helix protein. Helix-turn-helix proteins have a similar structure to bacterial regulatory proteins such as the 1 repressor and cro proteins, the lac repressor and so on which bind as dimers and their binding sites are palindromic. They contain 3 a helical regions separated by short turns which is why they are called helix-turn-helix proteins. One protein helix (helix 3) in each subunit of the dimer occupies the major groove of two successive turns of the DNA helix. Thus, in another embodiment, the disclosed polynucleotide-binding polypeptides can form dimers or other multi-component complexes, and have 1 to 3 helices.

In yet another embodiment, the modified polynucleotide-binding polypeptide includes a homeodomain or a portion of a homeodomain protein. Homeodomain proteins bind to a sequence of 180 base pairs initially identified in a group of genes called homeotic genes. Accordingly, the sequence was called the homeobox. The 180 bp corresponds to 60 amino acids in the corresponding protein. This protein domain is called the homeodomain. Homeodomain-containing proteins have since been identified in a wide range of organisms including vertebrates and plants. The homeodomain shows a high degree of sequence conservation. The homeodomain contains 4 α helical regions. Helices II and III are connected by 3 amino acids comprising a turn. This region has a very similar structure to helices II and III of bacterial DNA binding proteins.

Yet another embodiment provides a modified polynucleotide-binding polypeptide having a zinc finger domain or at least a portion of a zinc finger protein. Zinc finger proteins have a domain with the general structure: Phe (sometimes Tyr)-Cys-2 to 4 amino acids-Cys-3 amino acids-Phe (sometimes Tyr)-5 amino acids-Leu-2 amino acids-His-3 amino acids-His. The phenylalanine or tyrosine residues which occur at invariant positions are required for DNA binding. Similar sequences have been found in a range of other DNA binding proteins though the number of fingers varies. For example, the SP1 transcription factor which binds to the GC box found in the promoter proximal region of a number of genes has 3 fingers. This type of zinc finger which has 2 cysteines and 2 histidines is called a $C_2H_2$ Zinc finger.

Another type of zinc finger which binds zinc between 2 pairs of cysteines has been found in a range of DNA binding proteins. The general structure of this type of zinc finger is: Cys-2 amino acids-Cys-13 amino acids-Cys-2 amino acids-Cys. This is called a $C_2C_2$ zinc finger. It is found in a group of proteins known as the steroid receptor superfamily, each of which has 2 $C_2C_2$ zinc fingers.

Another embodiment provides a modified polynucleotide-binding polypeptide having a leucine zipper or at least a portion of a leucine zipper protein. The first leucine zipper protein was identified from extracts of liver cells, and it was called C/EBP because it is an enhancer binding protein and it was originally thought to bind to the CAAT promoter proximal sequence. C/EBP will only bind to DNA as a dimer. The region of the protein where the two monomers join to make the dimer is called the dimerization domain. This lies towards the C-terminal end of the protein. When the amino acid sequence was examined it was found that a leucine residue occurs every seventh amino acid over a stretch of 35 amino acids. If this region were to form an helix then all of these leucines would align on one face of the helix.

Because leucine has a hydrophobic side chain, one face of the helix is very hydrophobic. The opposite face has amino acids with charged side chains which are hydrophilic. The combination of hydrophobic and hydrophilic characteristics gives the molecule is amphipathic moniker. Adjacent to the leucine zipper region is a region of 20-30 amino acids which is rich in the basic (positively charged) amino acids lysine and arginine. This is the DNA binding domain—often referred to as the bZIP domain—the basic region of the leucine zipper. C/EBP is thought to bind to DNA by these bZIP regions wrapping round the DNA helix The leucine zipper—bZIP structure has been found in a range of other proteins including the products of the jun and fos oncogenes. Whereas C/EBP binds to DNA as a homodimer of identical subunits, fos cannot form homodimers at all and jun/jun homodimers tend to be unstable. However fos/jun heterodimers are much more stable. These fos/jun heterodimers correspond to a general transcription factor called AP1 which binds to a variety of promoters and enhancers and activates transcription. The consensus AP1 binding site is TGACTCA (SEQ. ID. NO.: 3) which is palindromic.

Another embodiment provides a modified polynucleotide-binding polypeptide having helix-loop-helix domain or a polynucleotide binding portion of a helix-loop-helix protein. Helix-loop-helix proteins are similar to leucine zippers in that they form dimers via amphipathic helices. They were first discovered as a class of proteins when a region of similarity was noticed between two enhancer binding proteins called E47 and E12. This conserved region has the potential to form two amphipathic separated by a loop hence helix-loop-helix. Next to the dimerization domain is a DNA binding domain, again rich in basic amino acids and referred to as the bHLH domain. These structures are also found in a number of genes required for development of the Drosophila nervous system—the Achaete-scute complex, and in a protein called MyoD which is required for mammalian muscle differentiation.

In still another embodiment, the modified polynucleotide binding polypeptide includes a histone polypeptide, a fragment of a histone polypeptide, or at least one histone fold. Histone folds exist in histone polypeptides monomers assembled into dimers. Histone polypeptides include H2A, H$_2$B, H3, and H4 which can form heterodimers H2A-2B and H3-H4. It will be appreciated that histone-like polypeptides can also be used in the disclosed compositions and methods. Histone-like polypeptides include, but are not limited to, HMf or the histone from Methanothermous fervidus, other archaeal histones known in the art, and histone-fold containing polypeptides such as MJ1647, CBF, TAFII or transcription factor IID, SPT3, and Dr1-DRAP (Sanderman, K. et al. (1998) CMLS. Cell. Mol. Life. Sci. 54:1350-1364, which is incorporated by reference in its entirety).

One embodiment, among others, provides a non-histone polynucleotide-binding polypeptide, for example a polynucleotide-binding polypeptide comprising mitochondrial transcription factor A (TFAM) polypeptide, a variant thereof, or a fragment thereof sufficient to bind polynucleotides. Variant TFAM can have 80%, 85%, 90%, 95%, 99% or greater sequence identity with a reference TFAM, for example naturally occurring TFAM.

TFAM is a member of the high mobility group (HMG) of proteins having two HMG-box domains. TFAM as well as other HMG proteins bind, wrap, bend, and unwind DNA. Thus, embodiments of the present disclosure include polynucleotide binding polypeptides comprising one or more polynucleotide binding regions of the HMG family of proteins, and optionally induce a structural change in the polynucleotide when the polypeptide binds or becomes associated with the polynucleotide. By inducing a conformational change in the polynucleotide, the polypeptide packages the polynucleotide. It has been reported that TFAM binds to mitochondrial DNA in a ratio of 900:1 (Alam, T. I. et al. (2003) Nucleic Acid Res. 31(6):1640-1645). It will be appreciated that the amount of polynucleotide-binding polypeptide used in the compositions and methods disclosed herein can vary depending on the size and amount of the polynucleotide to be delivered. Suitable ratios of polynucleotide-binding polypeptide to base pairs of polynucleotide to be delivered include, but are not limited to, about 1:1 to 1:1,000; more preferably 1:100; even more preferably 1: about 10 to about 20 base pairs of polynucleotide to be delivered. It will also be appreciated that TFAM, another polynucleotide-binding polypeptide, or a combination of two or more polynucleotide-binding polypeptides can be added to a polynucleotide to wrap or cover the polynucleotide, and thereby package the polynucleotide and protected it from degradation.

TFAM can be modified to include a PTD and optionally a targeting signal. The targeting signal can include a sequence of monomers that facilitates the localization of the molecule to a specific tissue, cell, or organelle. The monomers can be amino acids, nucleotide or nucleoside bases, or sugar groups such as glucose, galactose, and the like which form carbohydrate targeting signals.

B. Protein Transduction Domain

The polynucleotide-binding polypeptide can be modified to include a protein transduction domain (PTD), also known as cell penetrating peptides (CPPS). PTDs are known in the art, and include but are not limited to small regions of proteins that are able to cross a cell membrane in a receptor-independent mechanism (Kabouridis, P. (2003) Trends in Biotechnology (11):498-503). Although several of PTDs have been documented, the two most commonly employed PTDs are derived from TAT (Frankel and Pabo, (1988) Cell, December 23; 55(6): 1189-93) protein of HIV and Antennapedia transcription factor from Drosophila, whose PTD is known as Penetratin (Derossi et al., (1994) J Biol. Chem. 269(14): 10444-50).

The Antennapedia homeodomain is 68 amino acid residues long and contains four alpha helices (SEQ. ID NO. 4). Penetratin is an active domain of this protein which consists of a 16 amino acid sequence derived from the third helix of Antennapedia. TAT protein (SEQ. ID NO. 5) consists of 86 amino acids and is involved in the replication of HIV-1. The TAT PTD consists of an 11 amino acid sequence domain (residues 47 to 57; YGRKKRRQRRR (SEQ. ID. NO. 1)) of the parent protein that appears to be critical for uptake. Additionally, the basic domain Tat(49-57) or RKKRRQRRR (SEQ. ID NO. 2) has been shown to be a PTD. In the current literature TAT has been favored for fusion to proteins of interest for cellular import. Several modifications to TAT, including substitutions of Glutatmine to Alanine, i.e., Q→A, have demonstrated an increase in cellular uptake anywhere from 90% (Wender et al. 2000) to up to 33 fold in mammalian cells. (Ho et al. (2001) Cancer Res. 61(2):474-7) The most efficient uptake of modified proteins was revealed by mutagenesis experiments of TAT-PTD, showing that an 11 arginine stretch was several orders of magnitude more efficient as an intercellular delivery vehicle. Thus, some embodiments include PTDs that are cationic or amphipathic. Additionally exemplary PTDs include but are not limited to poly-Arg—RRRRRRR (SEQ. ID. NO.: 6); PTD-5—RRQRRTSKLMKR (SEQ. ID. NO.: 7); Transportan GWTLNSAGYLLGKINLKALAALAKKIL (SEQ. ID. NO.: 8); KALA—WEAKLAKALAKALA-KHLAKALAKALKCEA (SEQ. ID. NO.: 9); and RQIKIW-FQNRRMKWKK (SEQ. ID. NO.: 10).

C. Targeting Signal or Domain

In still other embodiments, the modified polynucleotide-binding polypeptide is optionally modified to include a targeting signal or domain. The targeting signal or sequence can be specific for a host, tissue, organ, cell, organelle, non-nuclear organelle, or cellular compartment. For example, the compositions disclosed herein can be modified with galactosyl-terminating macromolecules to target the compositions to the liver or to liver cells. The modified compositions selectively enter hepatocytes after interaction of the carrier galactose residues with the asialoglycoprotein receptor present in large amounts and high affinity only on these cells. Moreover, the compositions disclosed here can be targeted to other specific intercellular regions, compartments, or cell types.

In one embodiment, the targeting signal binds to its ligand or receptor which is located on the surface of a target cell such as to bring the vector and cell membranes sufficiently close to each other to allow penetration of the vector into the cell. Additional embodiments of the present disclosure are directed to specifically delivering polynucleotides to specific tissue or cell types, wherein the polynucleotides can encode a polypeptide or interfere with the expression of a different polynucleotide. The polynucleotides delivered to the cell can encode polypeptides that can enhance or contribute to the functioning of the cell.

In a preferred embodiment, the targeting molecule is selected from the group consisting of an antibody or antigen binding fragment thereof an antibody domain, an antigen, a T-cell receptor, a cell surface receptor, a cell surface adhesion molecule, a major histocompatibility locus protein, a viral envelope protein and a peptide selected by phage display that binds specifically to a defined cell.

Targeting polynucleotides to specific cells can be accomplished by modifying the disclosed compositions to express specific cell and tissue targeting signals. These sequences target specific cells and tissues, but in some embodiments the interaction of the targeting signal with the cell does not occur through a traditional receptor:ligand interaction. The eukaryotic cell comprises a number of distinct cell surface molecules. The structure and function of each molecule can be specific to the origin, expression, character and structure of the cell. Determining the unique cell surface complement of molecules of a specific cell type can be determined using techniques well known in the art.

One skilled in the art will appreciate that the tropism of the vector compositions described can be altered by merely changing the targeting signal. In one specific embodiment, compositions are provided that enable the addition of cell surface antigen specific antibodies to the vector for targeting the delivery of polynucleotides. Exemplary cell surface antigens are provided in Table 1 and described herein.

It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest i. Brain Targeting In one embodiment, the targeting signal is directed to cells of the nervous system, including the brain and peripheral nervous system. Cells in the brain include several types and states and possess unique cell surface molecules specific for the type. Furthermore, cell types and states can be further characterized and grouped by the presentation of common cell surface molecules.

In one embodiment, the targeting signal is directed to specific neurotransmitter receptors expressed on the surface of cells of the nervous system. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter or ligand capable of specifically binding to a neurotransmitter receptor.

In one embodiment, the targeting signal is specific to cells of the nervous system which may include astrocytes, microglia, neurons, oligodendrites and Schwann cells. These cells can be further divided by their function, location, shape, neurotransmitter class and pathological state. Cells of the nervous system can also be identified by their state of differentiation, for example stem cells Exemplary markers specific for these cell types and states are well known in the art and include, but are not limited to CD133 and Neurosphere.

ii. Muscle Targeting

In one embodiment, the targeting signal is directed to cells of the musculoskeletal system. Muscle cells include several types and possess unique cell surface molecules specific for the type and state. Furthermore, cell types and states can be further characterized and grouped by the presentation of common cell surface molecules.

In one embodiment, the targeting signal is directed to specific neurotransmitter receptors expressed on the surface of muscle cells. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter. Exemplary neurotransmitters expressed on muscle cells that can be targeted include but are not limited to acetycholine and norepinephrine, In one embodiment, the targeting signal is specific to muscle cells which consist of two major groupings, Type I and Type II. These cells can be further divided by their function, location, shape, myoglobin content and pathological state. Muscle cells can also be identified by their state of differentiation, for example muscle stem cells. Exemplary markers specific for these cell types and states are well known in the art include, but are not limited to MyoD, Pax7 and MR4.

iii. Tumor Targeting

In one embodiment, the targeting signal is used to selectively target tumor cells. Tumor cells express cell surface markers which may only be expressed in the tumor or present in non tumor cells but preferentially presented in tumor cells. Exemplary tumor specific cell surface markers include, but are not limited to, alfa-fetoprotein (AFP), C-reactive protein (CRP), cancer antigen-50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM. In one embodiment, the targeting signal consists of antibodies which are specific to the tumor cell surface markers.

iv. Antibodies

Another embodiment provides an antibody or antigen binding fragment thereof bound to the disclosed non-viral vectors acting as the targeting signal. The antibodies or antigen binding fragment thereof are useful for directing the vector to a cell type or cell state. In one embodiment, the vector possesses an antibody binding domain, for example from proteins known to bind antibodies such as Protein A and Protein G from *Staphylococcus aureus*. Other domains known to bind antibodies are known in the art and can be substituted. In certain embodiments, the antibody is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art.

In some embodiments, the targeting signal includes all or part of an antibody that directs the vector to the desired target cell type or cell state. Antibodies can be monoclonal or polyclonal, but are preferably monoclonal. For human gene therapy purposes, antibodies are derived from human genes and are specific for cell surface markers, and are produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

3. Modified Polypeptide:Polynucleotide Complexes

Modified polynucleotide-binding polypeptides having a protein transduction domain, and optionally, a targeting signal can be combined with a polynucleotide of interest to form a polypeptide-polynucleotide complex. For example, the modified polypeptide can reversibly bind the polynucleotide of interest. The binding or interaction between the modified polypeptide and the polynucleotide of interest is strong enough to protect the polynucleotide from degradation but reversible so that the polynucleotide maintains its biological activity once it has been delivered to the cell or organelle. The biological activity of the polynucleotide can include expressing the polypeptide encoded by the polynucleotide or the enzymatic activity of the polynucleotide if it is a ribozyme or DNAzyme.

In certain embodiments, one or more of the disclosed polynucleotide binding proteins can be combined with a polynucleotide of interest to package the polynucleotide for delivery into a cell. In particular, large polynucleotides having for example at least 1 kb, typically at least 10 kb to about 20 kb, or at least 30 kb can be packaged using the disclosed polypeptides. The polynucleotide binding protein can be added to a polynucleotide in amounts sufficient to package or condense the polynucleotide for delivery to a cell or host. The polypeptide can be added to the polynucleotide in a ratio of about 1 polypeptide to about 10 to about 100 nucleotides.

Another embodiment provides a method for transfecting a specific cell type or state by combining a polynucleotide-binding polypeptide, for example TFAM, with a polynucleotide to be delivered and an amount of a lipid and/or polyamine to form a complex and contacting a cell, for example a mammalian cell, with the complex. The polynucleotide-binding protein optionally includes a PTD and optionally a targeting signal. The lipid and/or polyamine can be branched or unbranched, saturated or unsaturated, and typically has a carbon chain length of about 6 to about 50 carbons, more typically about 10 to about 30 carbons, even more typically about 15 to about 20 carbons. The polynucleotide can be circular, for example a plasmid. The polynucleotide can also by multicistronic.

In one embodiment, the polynucleotide of interest is operably linked to a promoter or other regulatory elements known in the art. Thus, the polynucleotide can be a vector such as an expression vector. The promoter or regulatory element can drive expression of the polynucleotide in a cell type or state specific manner or under the control of a specific stimulus or molecule. The engineering of polynucleotides for expression in a prokaryotic or eukaryotic system may be performed by techniques generally known to those of skill in recombinant expression. It is believed that virtually any expression system may be employed in the expression of the disclosed nucleic and amino sequences.

An expression vector typically comprises one of the disclosed compositions under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors. It will be appreciated that any of these vectors may be packaged and delivered using one or more of the disclosed polynucleotide packaging polypeptides.

Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the disclosed compositions. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

One embodiment provides a modified TFAM polypeptide having at least one PTD, and optionally, at least one targeting signal. The modified TFAM can be associated with a polynucleotide of interest. The association can be accomplished in vitro or in vivo. TFAM can be mixed in amounts sufficient to wrap or bind the polynucleotide of interest. Typically, one molecule of TFAM wraps about 15 base pairs of a target polynucleotide. Enough modified TFAM can be added to a polynucleotide of interest to completely coat the exterior of the polynucleotide and/or to condense the polynucleotide. The polynucleotide is packaged so that the PTD and the optional targeting signal are displayed on the surface of the packaged polynucleotide. It will be appreciated that more than one polynucleotide can be packaged into a single complex using more than one modified polynucleotide-binding or packaging polypeptides.

The polynucleotide generally encodes a functional polypeptide, an antisense polynucleotide, or an inhibitory RNA and is packaged with the modified polynucleotide-binding polypeptide. At least one cell is contacted with the resulting complex either in vitro or in vivo. The targeting signal or domain facilitates the localization of the complex to a specific cell type or state, for example to the brain or a tumor. The protein transduction domain facilitates crossing the cell's outer membrane and delivers the polynucleotide to the interior of the cell. Once the polynucleotide of interest is delivered to its destination, it can be transcribed and ultimately translated. Alternatively, if the polynucleotide of interest is an antisense polynucleotide or enzymatic polynucleotide, the polynucleotide of interest can act at or near the deliver site, for example in the cytosol.

It has been reported that inhibitory polynucleotides are unstable in vivo, in part, because endogenous enzymes and immune responses actively degrade inhibitory polynucleotides, for example small inhibitory RNA (siRNA). siRNA technology is known in the art, and any siRNA, including single or multi-stranded siRNAs, can be used with the present disclosure. Thus, one embodiment of the present disclosure provides compositions and methods for delivering intact inhibitory RNA, for example siRNA, to a cell, tissue, or organ of interest. An siRNA can be combined with a polynucleotide-binding polypeptide having a protein transduction domain, and optionally, a targeting signal to form a complex. The modified polynucleotide-binding polypeptide can associate with the siRNA so that the siRNA is wrapped, covered, condensed, or bound by the modified polypeptide thereby protecting the siRNA from enzymatic degradation. The association is reversible such that upon delivery of the siRNA to the desired destination, the siRNA can function to inhibit the transcription or translation of its target polynucleotide.

Another exemplary embodiment provides a method for transfecting a host or a host's cell, including the steps of contacting a host's cell with a complex including a modified polynucleotide-binding polypeptide having at least one PTD, and optionally, at least one targeting signal, in combination with a polynucleotide of interest. In one embodiment, the polynucleotide-polypeptide complex acts as a non-viral vector. Cells from one host can be transfected and administered to a second host, or a hosts cells can be transfected and administered to the host. The transfection can occur in vivo or in vitro.

Suitable cells for transfection include cells capable of being transfected, for example eukaryotic or prokaryotic cells. The cells can be somatic, quiescent, embryonic, mitotic, stem cells, progenitor cells, germ line cells, pluripotent cells, totipotent cells, embryonic stem cells, heterologous cells, undifferentiated, partially differentiated, endoderm, mesoderm, ectoderm, immortalized, or primary cultures. Organelle targeting signals of the present disclosure include polypeptides having tropism for cell surface specific markers as those listed in Table 1. Suitable PTDs include but are not limited to HIV TAT YGRKKRRQRRR (SEQ. ID NO. 1) or RKKRRQRRR (SEQ. ID NO. 2); 11 Arginine residues, or positively charged polypeptides or polynucleotides having 8-15 residues, preferably 9-11 residues. It will be appreciated the disclosed compositions include a targeting signal, for example a cell type or state targeting signal, which causes the complex to associate with the cell type or state, typically via a receptor:ligand interaction. In one embodiment, the association of the targeting signal with the cell surface marker does not occur through a receptor:ligand interaction. The association of the cell surface marker and complex can be ionic, non-covalent, covalent, reversible or irreversible. Exemplary complex:cell surface marker associations include but are not limited to protein-protein, protein-carbohydrate, protein-nucleic acid, nucleic acid-nucleic acid, protein-lipid, lipid-carbohydrate, antibody-antigen, or avidin-biotin. The targeting signal of the complex can be a protein, peptide, antibody, antibody fragment, lipid, carbohydrate, biotin, avidin, steptavidin, chemical group, or other ligand that causes specific association between the cell type and state possessing the surface marker and complex, preferably an electromagnetic association as between oppositely charged moieties.

The specific interaction between the introduced complex and its target, for example a specific type of cell or cell state, can be accomplished by at least two methods. In one exemplary method a recombinant non-viral complex can include a recombinant polypeptide that expresses a targeting signal that interacts with the targeted cell type or state. Preferably, the complex expresses an outer polypeptide that is specific to the target cell type or state. In another method the complex is modified to incorporate an exogenous targeting protein to which a cell surface marker binds. Alternatively, a complex can include a modified recombinant polypeptide that specifically interacts with a desired cell, tissue, organ, or cell state, for example by expressing a amino acid sequence that interacts with the specific cell type or state. It will be appreciated by those of skill in the art that the complex can be chemically modified to have a net positive or negative charge depending on the modification agent. For example, the complex can be coated with polylysine or other agents containing a primary amino group. Additionally, amino groups can be linked to the complex or compound containing amino groups can be linked to the complex. The linkage can be reversible or irreversible, covalent or non-covalent. Other charged groups for conferring a charge to a compound are known in the art and can be incorporated into the complex.

Nucleic acids including but not limited to polynucleotides, anti-sense nucleic acids, peptide nucleic acids, natural or synthetic nucleic acids, nucleic acids with chemically modified bases, RNA, DNA, RNA-DNA hybrids, enzymatic nucleic acids such as ribozymes and DNAzymes, native/endogenous genes and non-native/exogenous genes and fragments or combinations thereof, can be introduced into a cell type or state. In one embodiment of the present disclosure, an inhibitory RNA can be directed to specific cell types or states. The inhibitory RNA can be introduced into the specific cell type or state with the complex when the complex interacts with the cell surface marker and crosses cell membrane via protein transduction domains.

Introduction of a polynucleotide into the cytosol of a eukaryotic cell, in an intact functional form, can be accomplished using standard techniques known to those skilled in the art or through modification of the recombinant polynucleotide-binding polypeptide with a protein transduction domains. Such transfection procedures include but are not limited to microinjection, electroporation, calcium chloride premeablization, polyethylene glycol permeabilization, protoplast fusion or cationic lipid premeablization. In one embodiment a polynucleotide-binding polypeptide is modified to include a Protein Transduction Domain that enables the polypeptide bound to a polynucleotide to be transduced across a lipid bilayer including a cellular membrane, organelle membrane, or plasma membrane. Suitable PTDs include but are not limited to an 11 Arginine PTD or Tat-PTD (SEQ. ID NOs. 3 or 4) and poly-Arg—RRRRRRR (SEQ. ID. NO.: 6); PTD-5—RRQRRTSKLMKR (SEQ. ID. NO.: 7); Transportan GWTLNSAGYLLGKINLKALAALAKKIL (SEQ. ID. NO.: 8); and KALA—WEAKLAKALAKALA-KHLAKALAKALKCEA (SEQ. ID. NO.: 9).

TABLE 1

Targeting Signals for Cell Types or Cell States.

| Cell Surface Antigen/Cell Type | Cell Ligand |
| --- | --- |
| Airway cells | Surfactant proteins A and B |
| Arterial wall | Artery wall binding peptide |
| ASGP receptor | Asialoglycoproteins |
| ASGP receptor | Synthetic galactosylated ligands |
| Carbohydrates | Lectins |
| CD3 | Anti-CD 3 |
| CD5 | Anti-CD 5 |
| CD44 | hyaluronic acid fragments |
| CD117 | Steel factor, Anti CD117 |
| EGF-R | EGF, EGF peptide Anti EGF-R, TGF-alpha |
| ErbB2 | anti ErbB2 |
| FcR | IgG |
| FGF2-R | basic FGF |
| Folate receptor | Folate |

TABLE 1-continued

Targeting Signals for Cell Types or Cell States.

| Cell Surface Antigen/Cell Type | Cell Ligand |
| --- | --- |
| Hepatocyte basolateral surface | Malarial circumsporozoite protein |
| Her2 | Anti HER2 |
| Insulin receptor | Insulin |
| Integrin | RGD peptide |
| LDL receptor family (hepatocytes) | Receptor associated protein (RAP) |
| Mannose receptor (macrophages) | Synthetic ligands, mannosylated |
| Nerve growth factor (NGF) receptor TrkA | NGF serived synthetic peptide |
| Neuroblastoma | Antibody ChCE7 |
| Ovarian carcinoma cell surface antigen OA3 | Antibody OV-TL16 Fab' fragment |
| PECAM (lung endothelium) | anti-PECAM antibody |
| Poly-immunoglobulin receptor | Anti-secretory component |
| Serpin-enzyme receptor | peptide ligand |
| Surface immunoglobulin | Anti-IgG, Anti-idiotype |
| Thrombomodulin | Anti-thrombomodulin |
| Tn carbohydrate | Anti-Tn |
| Transferrin receptor | Transferrin |
| Airway cells | Surfactant proteins A and B |
| Arterial wall | Artery wall binding peptide |
| ASGP receptor | Asialoglycoproteins |
| ASGP receptor | Synthetic galactosylated ligands |
| Carbohydrates | Lectins |

The nucleic acid and amino acid sequences for the disclosed targeting signals are known in the art. Table 2 below provides examples of the accession numbers from the NCID databases.

TABLE 2

| Signal | Accession Number | SEQ ID NO |
| --- | --- | --- |
| Lectin | AAA36170 | 11 |
| Transferrin | NP001054 | 12 |
| Insulin | AAA59172 | 13 |
| EGF | NP001954 | 14 |
| EGF Receptor | AAA52370 | 15 |
| TGF-alpha | NP003227 | 16 |

4. Exemplary Cells and Cell Lines

In another embodiment, the transfection complex comprises a recombinant polypeptide having a protein transduction domain and localization cell targeting signal in combination with a polynucleotide. The complex can be introduced into cytoplasm of cells from a heterogenous cell line possessing cells of different types, as in feeder cell culture, or in various states, as in differentiation. The cell line can be a transformed cell line that can be maintained indefinitely in cell culture, or the cell line can be a primary cell culture. Exemplary cell lines are those available from American Type Culture Collection including tumor cell lines which are incorporated herein by reference. The nucleic acid can be replicated and transcribed within the nucleus or cytoplasm of a cell of the transfected cell line.

Any eukaryotic cell can be transfected to produce cells that express a specific nucleic acid, for example a metabolic gene, including primary cells as well as established cell lines. Suitable types of cells include but are not limited to undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm. Suitable differentiated cells include somatic cells, neuronal cells, skeletal muscle, smooth muscle, pancreatic cells, liver cells, and cardiac cells.

In another embodiment, siRNA, antisense polynucleotides (including siRNA or antisense polynucleotides) or inhibitory RNA can be transfected into an cell using the compositions described herein.

5. Research Tools

In one embodiment, the present disclosure is used as a tool to investigate cellular consequences of gene expression. Mutant mice can be generated using this approach, allowing investigators to study various biological processes. More particularly, the methods and compositions disclosed herein can be used to generate cells that contain unique gene modifications known in the art and at the discretion of one skilled in the art.

6. Transgenic Non-Human Animals

The techniques described in the present disclosure can also be used to generate transgenic non-human animals. In particular, zygote microinjection, nuclear transfer, blastomere electrofision and blastocyst injection of embryonic stem (ES) cell cybrids have each provided feasible strategies for creating transgenic animals. In one embodiment an embryonic stem (ES) cell is transfected and injected into the blastocyst of a mammalian embryo as a means of generating chimeric mice. In another embodiment, embryonic stem (ES) cell are first prepared, followed by blastocyst injection into embryos. The use of cells carrying specific genes and modifications of interest allows the creation and study of the consequences of the transfected DNA. In theory, this technique offers the prospect of transferring any polynucleotide into a whole organism. For example, the disclosed methods and compositions could be used to create mice possessing the delivered polynucleotide in a specific cell type or cell state.

Another embodiment of the disclosure provides transfected non-human organisms and methods making and using them. Single or multicellular non-human organisms, preferably non-human mammals, more preferably mice, can be transfected with the compositions described herein by administering the compositions of the present disclosure to the non-human organism. In one embodiment, the polynucleotide remains episomal and does not stably integrate into the genome of the host organism. In another embodiment, the polynucleotide prevents the expression of a gene of interest. Thus, the expression of the polynucleotide in specific cells of the host can be controlled by the amount of polynucleotide administered to the host.

The disclosed transfected non-human organisms have several advantages over traditional transgenic organisms. For example, the transfected organism disclosed herein can be produced in less time that traditional transgenic organisms without sexual reproduction. Moreover, the expression of the polynucleotide of interest in the host can be directly regulated by the amount of polynucleotide of interest administered to the host. Dosage controlled expression of a polynucleotide of interest can be correlated to observed phenotypes and changes in the transfected animal. Additionally, inducible expression and/or replication control elements can be included in the polynucleotide of interest to provide inducible and dosage dependent expression and/or replication. Suitable inducible expression and/or replication control elements are known in the art. Furthermore, the effect of genes and gene modifications in specific cell types and states can be studied without affecting the entire cells of the animal.

7. Kits

The present disclosure is also directed to a kit or pack that supplies the elements necessary to conduct transfection of eukaryotic or prokaryotic organisms, in particular the transfection of specific cell types or cell states. In accordance with one embodiment a kit is provided comprising a DNA binding protein construct that includes a protein transduction domain and optionally, a targeting signal and domain. The protein construct can be combined with an antibody of the users choosing to direct the vector complex to specific cell types or states determined by the antibody. The protein is further mixed with the polynucleotide to form a complex which can be used to transfect a host or a host cell. In another embodiment the protein construct provided with the kit comprises localization targeting signal selected from those known to target to a cell type or cell state, partially listed in Table I. In accordance with one embodiment a kit is provided comprising cells that express the protein construct. The cells can be cultured to produce the protein construct in large quantities which can be harvested, purified, and concentrated. The individual components of the kits can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

In one embodiment, the kit includes a construct having a polynucleotide binding domain that hybridizes or binds to a predetermined nucleic acid sequence. In another embodiment, kit includes a polynucleotide-binding polypeptide that non-specifically hybridizes or binds to polynucleotides of interest.

8. Genetic Diseases or Syndromes

Embodiments of the present disclosure provide compositions and methods applicable for gene therapy protocols and the treatment of gene related diseases or disorders. Cell dysfunction can also be treated or reduced using the disclosed compositions and methods. In particular, diseases amenable to gene therapy are specifically targeted. The disease can be in children, for example individuals less that 18 years of age, typically less than 12 years of age, or adults, for example individuals 18 years of age or more. Thus, embodiments of the present disclosure are directed to treating a host diagnosed with a disease, in particular a genetic disease, by introducing a vector into the host cell wherein the vector specifically binds to the cell type or cell state affected by the disease and wherein the vector comprises a nucleic acid encoding a therapeutic protein. In another embodiment, an inhibitory RNA is directed to a specific cell type or state to reduce or eliminate the expression of a protein, thereby achieving a therapeutic effect. The present disclosure encompasses manipulating, augmenting or replacing genes to treat diseases caused by genetic defects or abnormalities.

Suitable genetic based disease that can be treated with the compositions disclosed herein include but are not limited to:

Mitochondrial Disease: Alpers Disease; Barth syndrome; β-oxidation defects; carnitine-acyl-carnitine deficiency; carnitine deficiency; co-enzyme Q10 deficiency; Complex I deficiency; Complex II deficiency; Complex III deficiency; Complex IV deficiency; Complex V deficiency; cytochrome c oxidase (COX) deficiency, LHON—Leber Hereditary Optic Neuropathy; MM—Mitochondrial Myopathy; LIMM—Lethal Infantile Mitochondrial Myopathy; MMC—Maternal Myopathy and Cardiomyopathy; NARP—Neurogenic muscle weakness, Ataxia, and Retinitis Pigmentosa; Leigh Disease; FICP—Fatal Infantile Cardiomyopathy Plus, a MELAS-associated cardiomyopathy; MELAS—Mitochondrial Encephalomyopathy with Lactic Acidosis and Stroke-like episodes; LDYT—Leberrs hereditary optic neuropathy and Dystonia; MERRF—Myoclonic Epilepsy and Ragged Red Muscle Fibers; MHCM—Maternally inherited Hypertrophic CardioMyopathy; CPEO—Chronic Progressive External Opthalmoplegia; KSS—Kearns Sayre Syndrome; DM—Diabetes Mellitus; DMDF Diabetes Mellitus+DeaFness; CIPO—Chronic Intestinal Pseudoobstruction with myopathy and Opthalmoplegia; DEAF—Maternally inherited DEAFness or aminoglycoside-induced DEAFness; PEM—Progressive encephalopathy; SNHL—SensoriNeural Hearing Loss; Encephalomyopathy; Mitochondrial cytopathy; Dilated Cardiomyopathy; GER—Gastrointestinal Reflux; DEMCHO—Dementia and Chorea; AMDF—Ataxia, Myoclonus; Exercise Intolerance; ESOC Epilepsy, Strokes, Optic atrophy, & Cognitive decline; FBSN Familial Bilateral Striatal Necrosis; FSGS Focal Segmental Glomerulosclerosis; LIMM Lethal Infantile Mitochondrial Myopathy; MDM Myopathy and Diabetes Mellitus; MEPR Myoclonic Epilepsy and Psychomotor Regression; MERME MEREF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephalocardiomyopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young.

Nuclear Disease: Muscular Dystrophies, Ellis-van Creveld syndrome, Marfan syndrome, Myotonic dystrophy, Spinal muscular atrophy, Achondroplasia, Amyotrophic lateral sclerosis, Charcot-Marie-Tooth syndrome, Cockayne syndrome, Diastrophic dysplasia, Duchenne muscular dystrophy, Ellis-van Creveld syndrome, Fibrodysplasia ossificans progressive, Alzheimer disease, Angelman syndrome, Epilepsy, Essential tremor, Fragile X syndrome, Friedreich's ataxia, Huntington disease, Niemann-Pick disease, Parkinson disease, Prader-Willi syndrome, Rett syndrome, Spinocerebellar atrophy, Williams syndrome, Ataxia telangiectasia, Anemia, sickle cell, Burkitt lymphoma, Gaucher disease, Hemophilia, Leukemia, Paroxysmal nocturnal hemoglobinuria, Porphyria, Thalassemia, Crohn's disease, Alpha-1-antitrypsin deficiency, Cystic fibrosis, Deafness, Pendred syndrome, Glaucoma, Gyrate atrophy of the choroid and retina, Adrenal hyperplasia, Adrenoleukodystrophy, Cockayne syndrome, Long QT syndrome, Immunodeficiency with hyper-IgM, Alport syndrome, Ellis-van Creveld syndrome, Fibrodysplasia ossificans progressive, Waardenburg syndrome, Werner syndrome.

Infectious Disease Viral—AIDS, AIDS Related Complex, Chickenpox (Varicella), Common cold, Cytomegalovirus Infection, Colorado tick fever, Dengue fever, Ebola haemorrhagic fever, Epidemic parotitis, Flu, Hand, foot and mouth disease, Hepatitis—Herpes simplex, Herpes zoster, HPV, Influenza, Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease—Yellow fever; Bacterial—Anthrax, Bacterial Meningitis, Brucellosis, Bubonic plague, Campylobacteriosis, Cat Scratch Disease, Cholera, Diphtheria, Epidemic Typhus, Gonorrhea, Hansen's Disease, Legionellosis, Leprosy, Leptospirosis, Listeriosis, Lyme Disease, Melioidosis, MRSA infection, Nocardiosis, Pertussis, Pneumococcal pneumonia, Psittacosis, Q fever, Rocky Mountain Spotted Fever or RMSF, Salmonellosis, Scarlet Fever, Shigellosis, Syphilis, Tetanus, Trachoma, Tuberculosis, Tularemia, Typhoid Fever, Typhus, Whooping Cough; Parasitic—African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trypanosomiasis.

Cancers: Breast and ovarian cancer, Burkitt lymphoma, Chronic myeloid leukemia, Colon cancer, Lung cancer, Malignant melanoma, Multiple endocrine neoplasia, Neurofibromatosis, p53 LieFrauMeni, Pancreatic cancer, Prostate cancer, retinoblastoma, von Hippel-Lindau syndrome, Polycystic kidney disease, Tuberous sclerosis.

Metabolic Disorders: Adrenoleukodystrophy, Atherosclerosis, Best disease, Gaucher disease, Glucose galactose malabsorption, Gyrate atrophy, Juvenile onset diabetes, Obesity, Paroxysmal nocturnal hemoglobinuria, Phenylketonuria, Refsum disease, Tangier disease, Tay-Sachs disease, Adrenoleukodystrophy, Type 2 Diabetes, Gaucher disease, Hereditary hemochromatosis, Lesch-Nyhan syndrome, Maple syrup urine disease, Menkes syndrome, Niemann-Pick disease, Pancreatic cancer, Prader-Willi syndrome, Porphyria, Refsum disease, Tangier disease, Wilson's disease, Zellweger syndrome, progerias, SCID.

Autoimmune Disorders: Autoimmune polyglandular syndrome, lupus, type I diabetes, scleroderma, multiple sclerosis, Crohn's disease, chronic active hepatitis, rheumatoid arthritis, Graves' disease, myasthenia gravis, myositis, antiphospholipid syndrome (APS), uveitis, polymyositis, Raynaud's phenomenon, and demyelinating neuropathies, and rare disorders such as polymyalgia rheumatica, temporal arteritis, Sjogren's syndrome, Bechet's disease, Churg-Strauss syndrome, and Takayasu's arteritis.

Inflammatory Disorders: Alopecia, Diastrophic dysplasia, Ellis-van Creveld syndrome, Asthma, Arthritis, including osteoarthritis, rheumatoid arthritis, and spondyloarthropathies.

Age-Related Disorders: Alzheimer Disease, Parkinson's Disease, Atherosclerosis, Age-Related Macular Degeneration, Age-related Osteoporosis. The disclosed methods and compositions can also be used to treat, manage, or reduce symptoms associated with aging, in tissue regeneration/regenerative medicine, stem cell transplantation, inducing reversible genetic modifications, expressing inhibitory RNA, cognitive enhancement, performance enhancement, and cosmetic alterations to human or non-human animal.

9. Administration

The compositions provided herein may be administered in a physiologically acceptable carrier to a host. Preferred methods of administration include systemic or direct administration to a cell. The compositions can be administered to a cell or patient, as is generally known in the art for gene therapy applications. In gene therapy applications, the compositions are introduced into a host in order to transfect specific cell types or cell states. "Gene therapy" includes both conventional gene therapy where a lasting effect is achieved by a single treatment, and the administration of gene therapeutic agents, which involves the one time or repeated administration of a therapeutically effective DNA or RNA.

The modified complex compositions can be combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween®, Pluronics® or PEG.

The compositions of the present disclosure can be administered parenterally. As used herein, "parenteral administration" is characterized by administering a pharmaceutical composition through a physical breach of a subject's tissue. Parenteral administration includes administering by injection, through a surgical incision, or through a tissue-penetrating non-surgical wound, and the like. In particular, parenteral administration includes subcutaneous, intraperitoneal, intravenous, intraarterial, intramuscular, intrasternal injection, and kidney dialytic infusion techniques.

Parenteral formulations can include the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Parenteral administration formulations include suspensions, solutions, emulsions in oily or aqueous vehicles, pastes, reconsitutable dry (i.e. powder or granular) formulations, and implantable sustained-release or biodegradable formulations. Such formulations may also include one or more additional ingredients including suspending, stabilizing, or dispersing agents. Parenteral formulations may be prepared, packaged, or sold in the form of a sterile injectable aqueous or oily suspension or solution. Parenteral formulations may also include dispersing agents, wetting agents, or suspending agents described herein. Methods for preparing these types of formulations are known. Sterile injectable formulations may be prepared using non-toxic parenterally-acceptable diluents or solvents, such as water, 1,3-butane diol, Ringer's solution, isotonic sodium chloride solution, and fixed oils such as synthetic monoglycerides or diglycerides. Other parentally-administrable formulations include microcrystalline forms, liposomal preparations, and biodegradable polymer systems. Compositions for sustained release or implantation may include pharmaceutically acceptable polymeric or hydrophobic materials such as emulsions, ion exchange resins, sparingly soluble polymers, and sparingly soluble salts.

Pharmaceutical compositions may be prepared, packaged, or sold in a buccal formulation. Such formulations may be in the form of tablets, powders, aerosols, atomized solutions, suspensions, or lozenges made using known methods, and may contain from about 0.1% to about 20% (w/w) active ingredient with the balance of the formulation containing an orally dissolvable or degradable composition and/or one or more additional ingredients as described herein. Preferably, powdered or aerosolized formulations have an average particle or droplet size ranging from about 0.1 nanometers to about 200 nanometers when dispersed.

As used herein, "additional ingredients" include one or more of the following: excipients; surface active agents, dispersing agents, inert diluents, granulating agents, disintegrating agents, binding agents, lubricating agents, sweetening agents, flavoring agents, coloring agents, preservatives, physiologically degradable compositions (e.g., gelatin), aqueous vehicles, aqueous solvents, oily vehicles and oily solvents, suspending agents, dispersing agents, wetting agents, emulsifying agents, demulcents, buffers, salts, thickening agents, fillers, emulsifying agents, antioxidants, antibiotics, antifungal agents, stabilizing agents, and pharmaceutically acceptable polymeric or hydrophobic materials. Other "additional ingredients" which may be included in the pharmaceutical compositions are known. Suitable additional ingredients are described in Remington's Pharmaceutical Sciences, Mack Publishing Co., Genaro, ed., Easton, Pa. (1985).

Dosages and desired concentrations modified vectors disclosed herein in pharmaceutical compositions of the present disclosure may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J, and Chappell, W. "The use of interspecies scaling in toxicokinetics" In Toxicokinetics and New Drug Development, Yacobi et al., Eds., Pergamon Press, New York 1989, pp. 42-96.

EXAMPLES

Example 1

Recombinant Constructs

The 11 amino acid protein transduction domain (PTD) consisting of 11 arginines was cloned in frame to the antibody binding portion, domain B, of Protein A from *Staphylococcus aureus*. The PTD-Domain B coding sequence was cloned in tandem upstream of the TFAM coding sequence and cloned into a bacterial expression vector. The recombinant protein was expressed in bacteria and isolated. Purified protein was concentrated and protein concentration was assessed with the Bradford Assay (Biorad). Purified protein was analyzed with SDS-Page to verify purity.

Example 2

Construct Sequence Data

PTD-PA-TFAM (PTD solid underline; Tandem Domain B of Protein A Antibody Binding Domain double underline; TFAM dash underline) peptide Length (332):

```
    MRRRRRRRRRRRGEGDIMGEWGNEIFGAIAGFLGGEHDEAQQN
AFYQVLNMPNLNADQRNGFIQSLKDDPSQSANVLGEAHDEAQQNAFYQ
VLNMPNLNADQRNGFIQSLKDDPSQSANVLGEAGEGSSVLASCPKKPVS
SYLRFSKEQLPIFKAQNPDAKTTELIRRIAQRWRELPDSKKKIYQDAYRA
EWQVYKEEISRFKEQLTPSQIMSLEKEIMDKHLKRKAMTKKKELTLLGK
PKRPRSAYNVYVAERFQEAKGDSPQEKLKTVKENWKNLSDSEKELYIQ
HAKEDETRYHNEMKSWEEQMIEVGRKDLLRRTIKKQRKYGAEEC (SEQ
ID NO:17)
```

Selected Model Organism Protein Similarities That Can Be Used In The Compositions And Methods Disclosed Herein:

Organism, Protein and Percent Identity and Length of Aligned Region

| | | |
|---|---|---|
| *H. sapiens* (SEQ. ID. NO.: 18): | sp: Q00059 - MTT1_HUMAN Transcription factor 1, mitochondrial precursor (MTTF1) | 100%/246 aa (see ProtEST) |
| *M. musculus* (SEQ. ID. NO.: 19): | ref: NP_033386.1 - transcription factor A, mitochondrial [*Mus musculus*] | 63%/237 aa (see ProtEST) |

| | | | |
|---|---|---|---|
| R. norvegicus: (SEQ. ID. NO.: 20): | ref: NP_112616.1 - transcription factor A, mitochondrial [Rattus norvegicus] | 64%/237 aa (see ProtEST) | |
| A. thaliana (SEQ. ID. NO.: 21):: | ref: NP_192846.1 - 98b like protein [Arabidopsis thaliana] | 27%/189 aa (see ProtEST) | |
| C. elegans (SEQ. ID. NO.: 22):: | ref: NP_501245.1 - F45E4.9.p [Caenorhabditis elegans] | 27%/189 aa (see ProtEST) | |
| D. melanogaster: (SEQ. ID. NO.: 23): | ref: NP_524415.1 - mitochondrial transcription factor A [Drosophila melanogaster] | 34%/183 aa (see ProtEST) | |

Sequence data for the sequences referenced herein are known in the art, for example in GenBank, and are incorporated by reference herein, in their entirety.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A method for delivering a polynucleotide to one or more cells the method comprising:
contacting the one or more cells with the polynucleotide packaged with a mitochondrial transcription factor A (TFAM) polypeptide fusion protein comprising a protein transduction domain, a cell-specific targeting signal and the TFAM polypeptide wherein the TFAM polypeptide comprises two HMG box domains and binds the polynucleotide.

2. The method of claim 1, wherein the targeting signal provides tropism for the fusion protein to a target cell type or a target cell state.

3. The method of claim 2, wherein the targeting signal comprises a portion of bacterial Protein A sufficient to bind an Fc portion of a mammalian antibody.

4. The method of claim 3, wherein the portion of Protein A is operably linked to an antibody specific for a cell surface antigen.

5. The method of claim 4, wherein the antibody provides the tropism for the fusion protein to a target cell type or a target cell state.

6. The method of claim 2, wherein the targeting signal comprises a polypeptide from a protein or a peptide comprising the targeting signal wherein the protein or the peptide is selected from the group consisting of a Surfactant protein A, a surfactant protein B, an Artery wall binding peptide, an Asialoglycoprotein, a Synthetic galactosylated ligand, a Lectin, an Anti-CD 3 antibody, an Anti-CD 5 antibody, a hyaluronic acid fragment, a Steel factor, an Anti CD 117 antibody, an EGF peptide, an Anti EGF-R antibody, a TGF-alpha, an anti ErbB2 antibody, an IgG, a basic FGF, a Folate, a Malarial circumsporozoite protein, an Anti HER2 antibody, an Insulin, an RGD peptide, a Receptor associated protein (RAP), a Synthetic ligand, a mannosylated synthetic ligand, an NGF derived synthetic peptide, an Antibody ChCE7, an Antibody OV-TL16 Fab' fragment, an anti-PECAM antibody, an Anti-secretory component, an Anti-IgG antibody an Anti-idiotype antibody, an Anti-thrombomodulin antibody, an Anti-Tn antibody, and a Transferrin.

7. The method of claim 6, wherein the contacting occurs in vitro or in vivo.

8. The method of claim 1, wherein the contacting occurs in vitro or in vivo.

9. The method of claim 1, wherein the TFAM fusion protein comprises the amino acids of SEQ ID NO: 17.

10. The method of claim 1, wherein the TFAM fusion protein further comprises the mitochondrial localization signal of superoxide dismutase (Mn).

* * * * *

UNITED STATES PATENT AND TRADEMARK OFFICE
CERTIFICATE OF CORRECTION

PATENT NO. : 8,133,733 B2
APPLICATION NO. : 11/932674
DATED : March 13, 2012
INVENTOR(S) : Shaharyar Khan It is certified that error appears in the above-identified patent and that said Letters Patent is hereby corrected as shown below:

Specification, column 1, lines 18-20, replace "Aspects of the following disclosure were supported in part by NIH-NIA SBIR grant number AG022780. Therefore, the United States has certain rights in the disclosure." with --This invention was made with government support under Grant Number AG022780, awarded by the National Institutes of Health-National Institute on Aging Small Business Innovation Research (NIH-NIA SBIR). The government has certain rights in the invention--.

Claim 6, column 56, line 65, replace "antibody an Anti-Idiotype" with --antibody, an Anti-idiotype--.

Signed and Sealed this
Sixth Day of November, 2012

David J. Kappos
*Director of the United States Patent and Trademark Office*